(12) United States Patent
Sochor

(10) Patent No.: US 8,968,331 B1
(45) Date of Patent: Mar. 3, 2015

(54) IMPLANTABLE LEAD AND SURGICAL ACCESSORIES

(76) Inventor: Jerzy Roman Sochor, Sunnyvale, CA (US)

(*) Notice: Subject to any disclaimer, the term of this patent is extended or adjusted under 35 U.S.C. 154(b) by 1349 days.

(21) Appl. No.: 12/766,867

(22) Filed: Apr. 24, 2010

(51) Int. Cl.
*A61B 19/00* (2006.01)

(52) U.S. Cl.
USPC ........................................ 606/129

(58) Field of Classification Search
CPC .. A61B 5/042; A61B 2018/1405; A61N 1/04; A61N 1/05; A61N 1/0529; A61N 1/0531; A61N 1/0534; A61N 2001/0578
USPC ........... 606/129; 607/116; 600/372, 373, 378; 604/166.01
See application file for complete search history.

(56) References Cited

U.S. PATENT DOCUMENTS

| | | | |
|---|---|---|---|
| 5,843,148 A | 12/1998 | Gijsbers et al. | |
| 6,413,263 B1 | 7/2002 | Lobdill et al. | |
| 6,477,427 B1 | 11/2002 | Stolz et al. | |
| 6,606,521 B2 | 8/2003 | Paspa et al. | |
| 7,033,326 B1 | 4/2006 | Pianca et al. | |
| 7,450,997 B1 | 11/2008 | Pianca et al. | |
| 7,454,251 B2 | 11/2008 | Rezai et al. | |

*Primary Examiner* — Katherine Dowe

(57) ABSTRACT

Leads for chronic implantation in the brain or other anatomical targets utilize tubular stylet means which are external to the lead. The lead comprises a distal electrode terminal, a proximal connector terminal, and a conductor cable having a reinforced distal portion and a stepped outside diameter providing a shoulder which cooperates with the distal end of the external stylet means. The substantial stiffness of the external stylet allows implantation of the lead without a brain-entering cannula. A tubular stylet spacer is employed to minimize lead dislodgement due to disassembly and removal of the lead introduction tools. Externalized stylet allows the conductor cable to have a small outside diameter and a desirably short length. A method of terminating conductors to electrodes using inserts is suitable for very fine wires and stranded conductors. A reinforced electrode terminal construction enables robust small-dimensioned terminal and high localization accuracy when introduced with external stylet means.

58 Claims, 28 Drawing Sheets

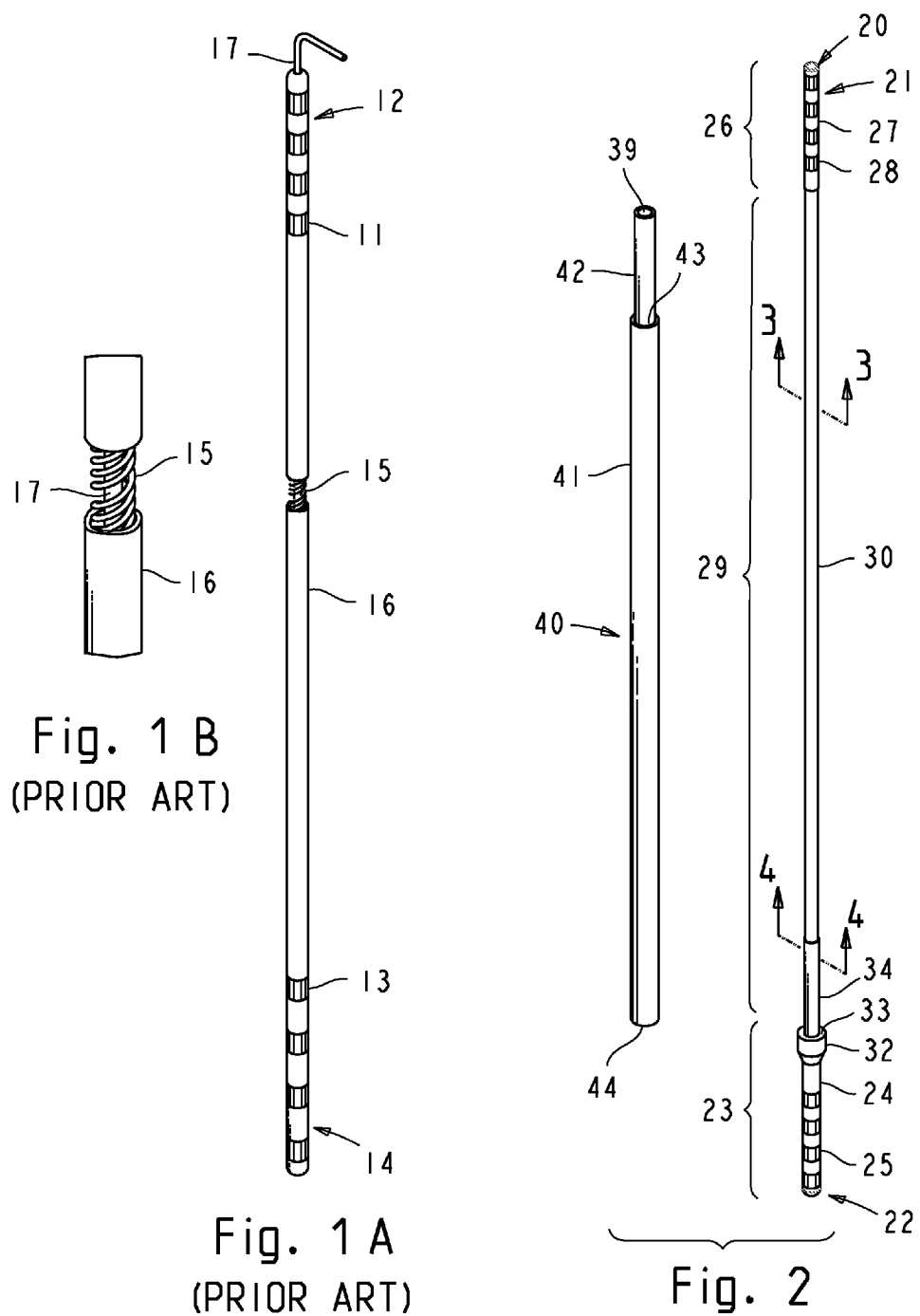

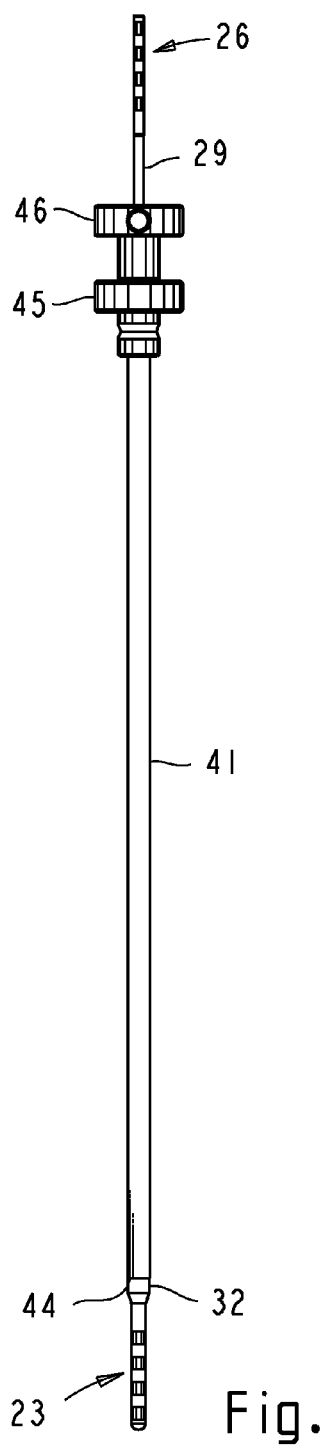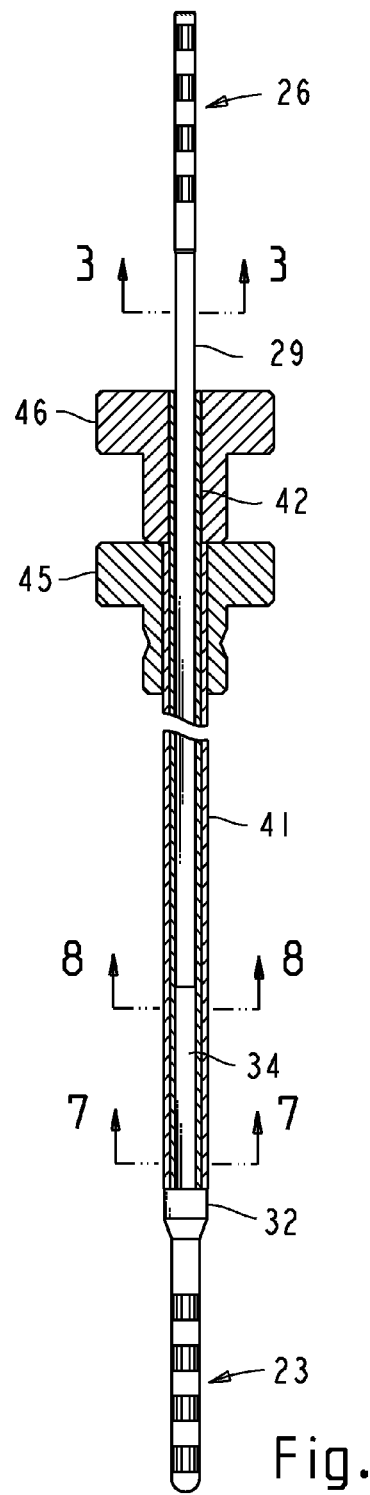
Fig. 5 A  Fig. 5 B

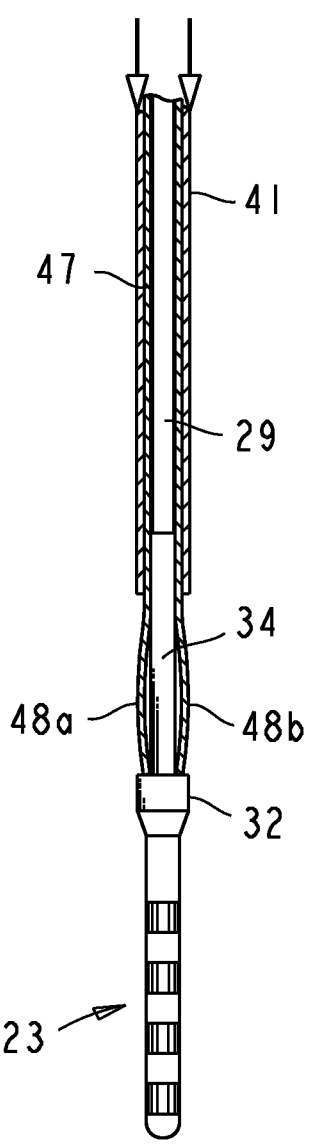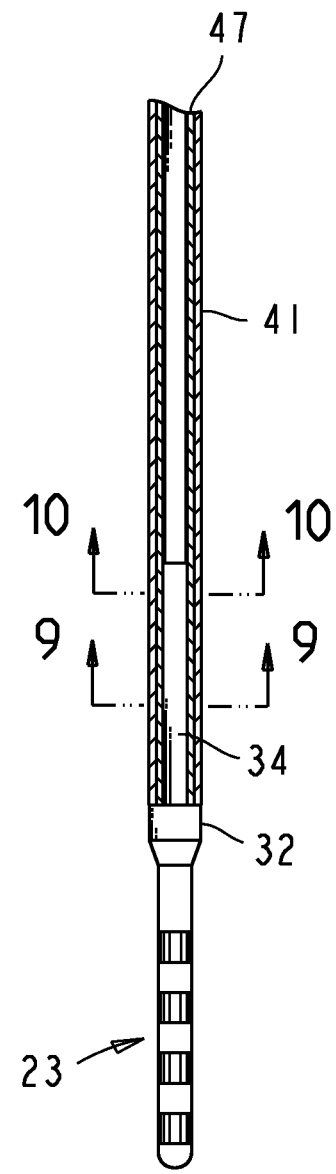
Fig. 6 A  Fig. 6 B

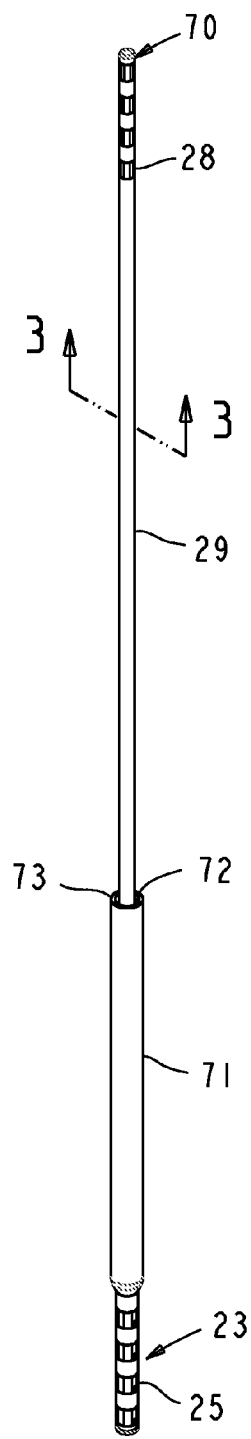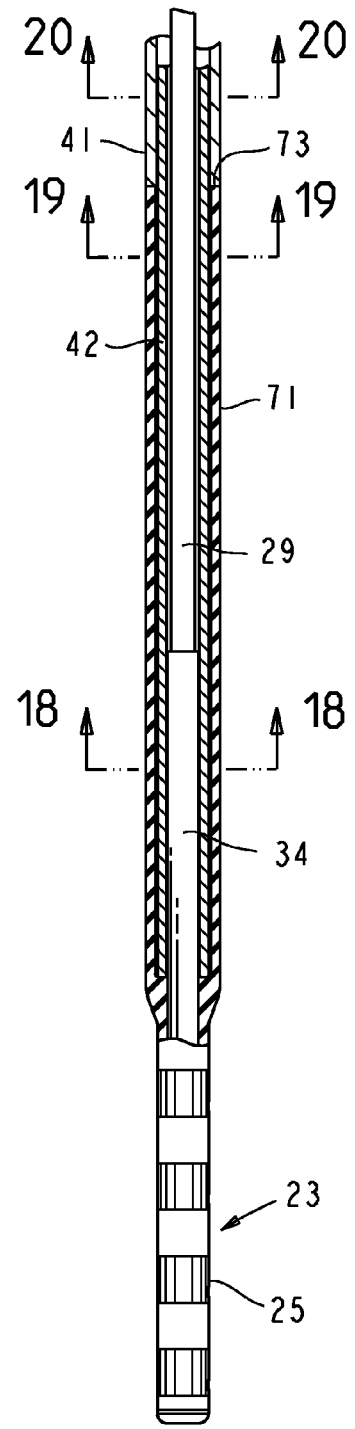
Fig. 17 A
Fig. 17 B

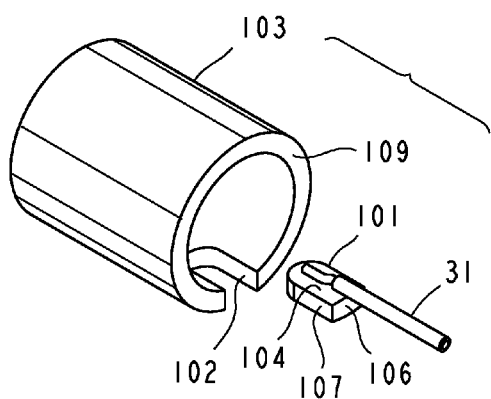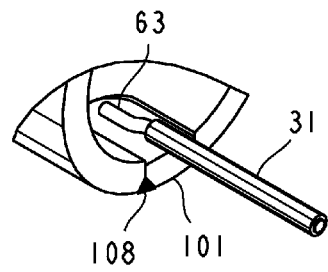
Fig. 28 A    Fig. 28 B
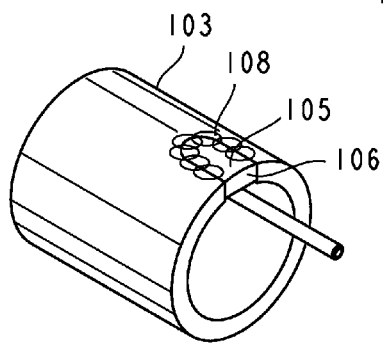
Fig. 28 C
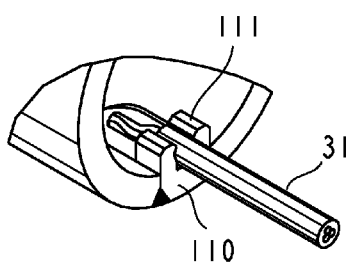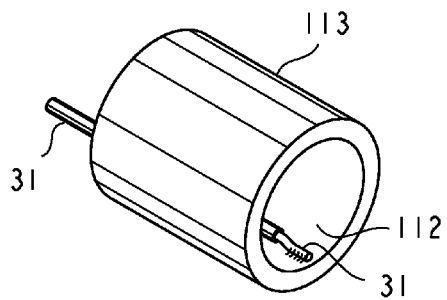
Fig. 29    Fig. 30

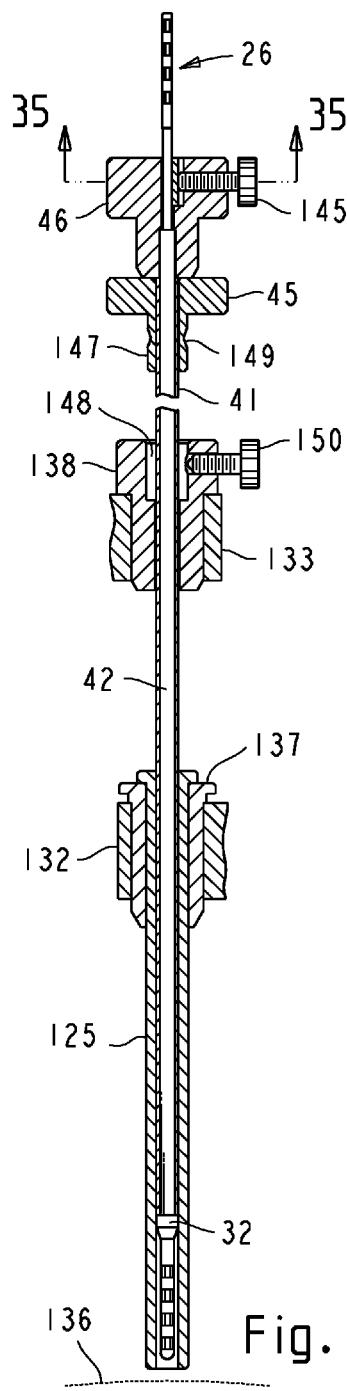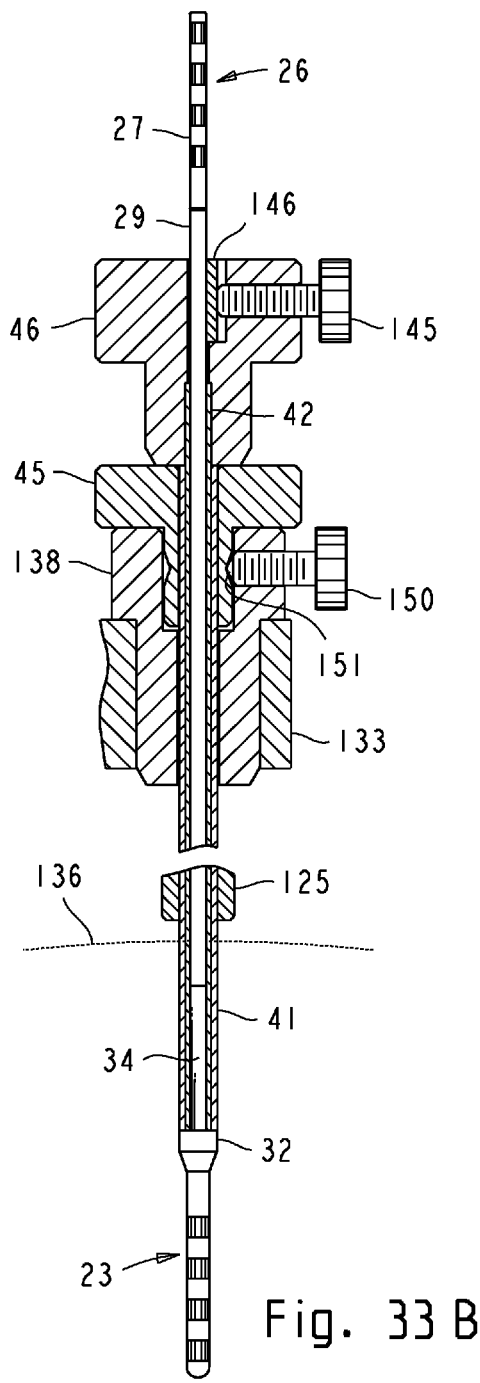
Fig. 33 A    Fig. 33 B

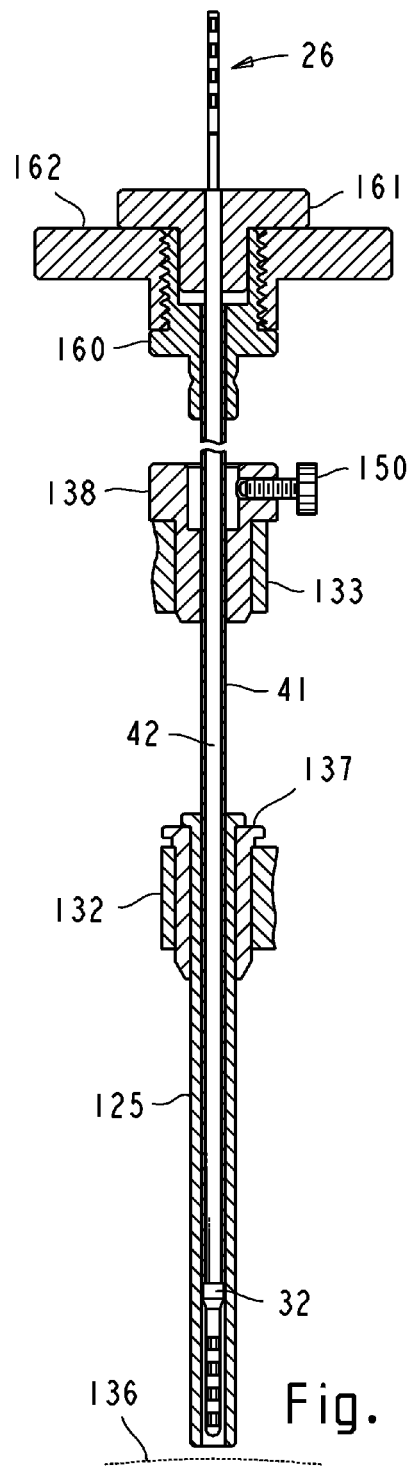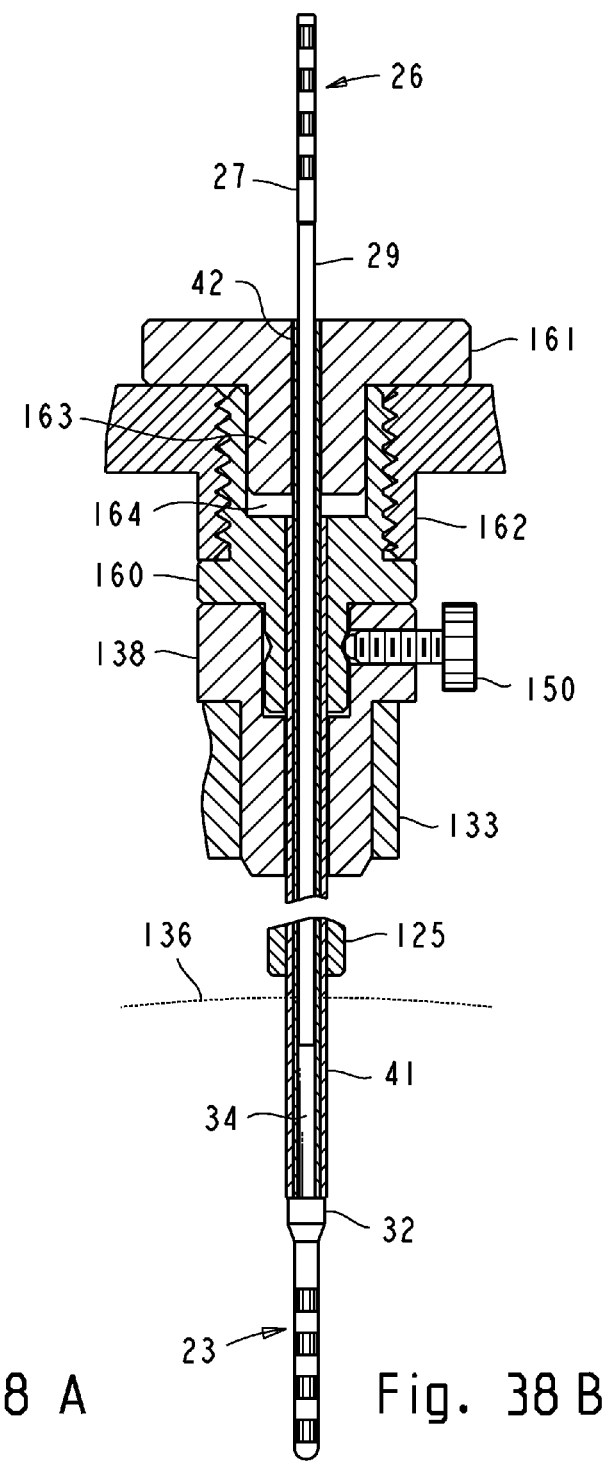
Fig. 38 A  Fig. 38 B

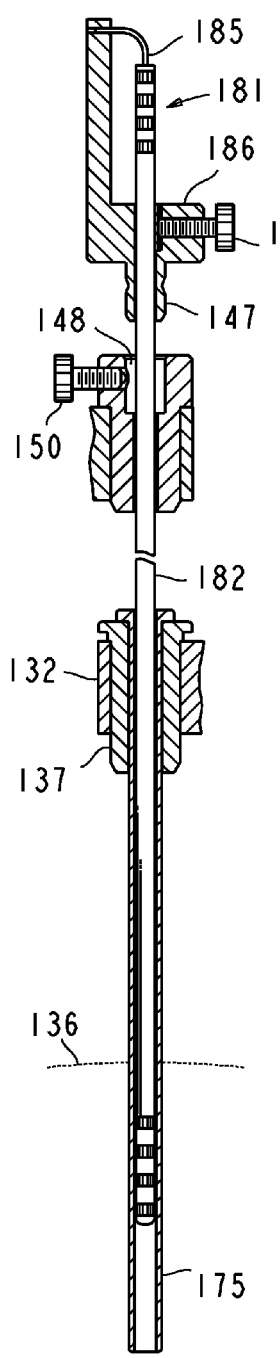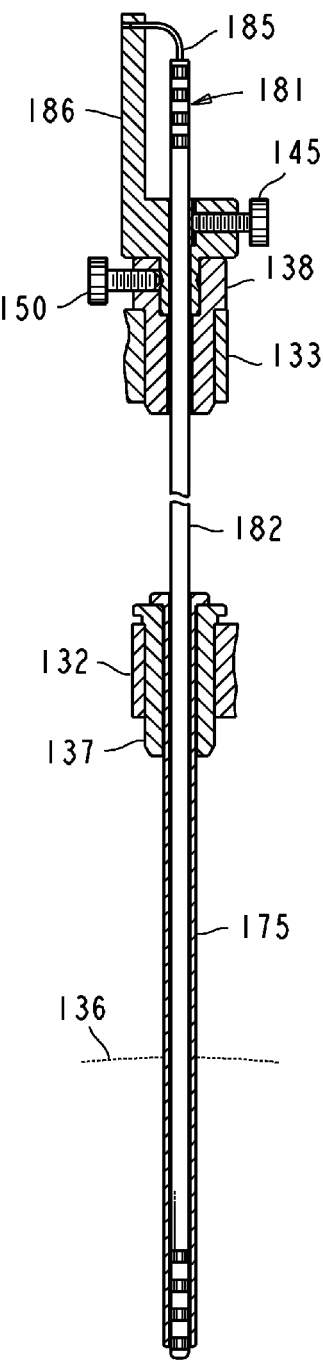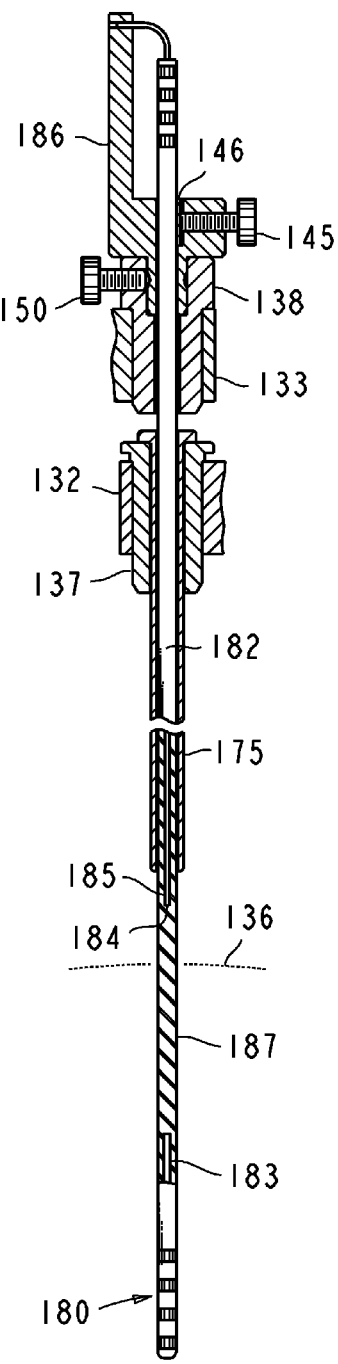
Fig. 45 A          Fig. 45 B          Fig. 45 C

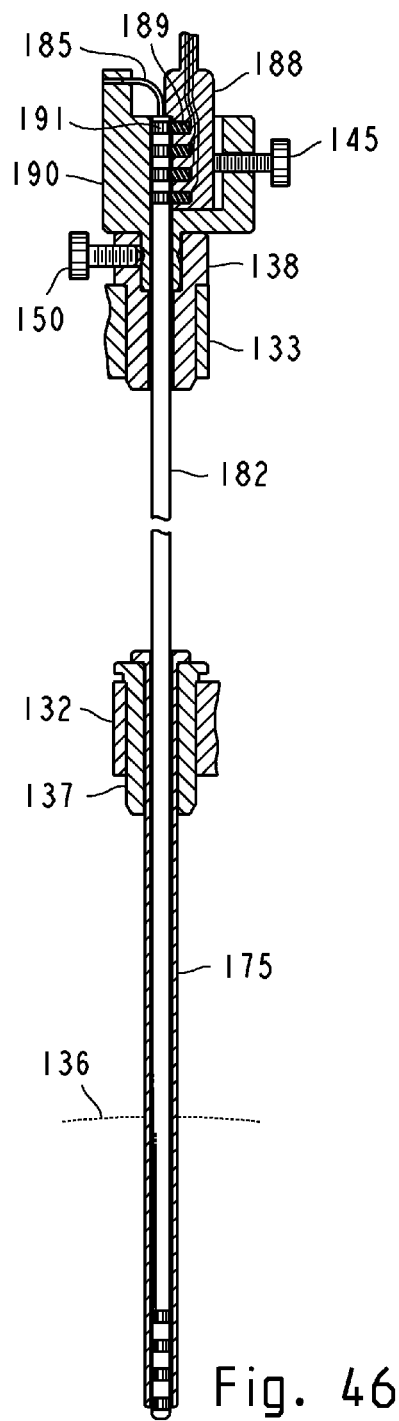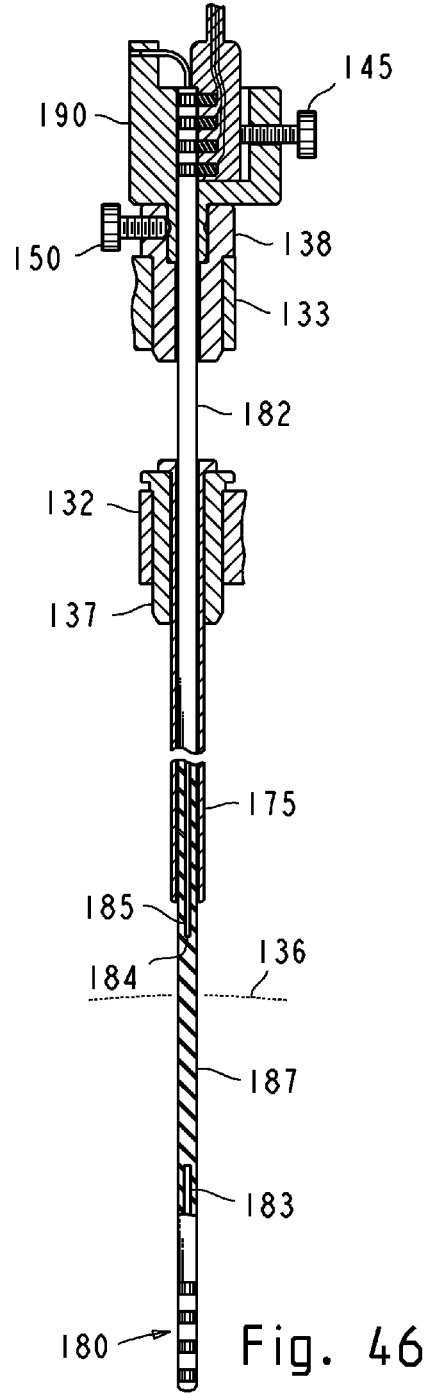
Fig. 46 A    Fig. 46 B

IMPLANTABLE LEAD AND SURGICAL ACCESSORIES

BACKGROUND

Prior Art

Electrical stimulation of brain is an important therapy for treatment of movement disorders such as Parkinson's disease and epilepsy and has been proposed for numerous other conditions, such as chronic pain and psychiatric disorders. Cochlear stimulation is being used to allow profoundly deaf patients to experience sensation of hearing. Other uses of electrical sensing and stimulation of neural and other tissue include sensing and regulating physiological activity and development of stimulators designed to enable use of lost or impaired body functions, e.g., ability to see.

Electrical stimulation is delivered by an implantable medical device, e.g., a neurostimulator, which is surgically implanted within the cranium, the chest, or other part of the body. The device has at least one implantable electrical lead connected to it, which transmits electrical stimuli that are used to modulate and/or sense tissue activity. The lead has one or more sensing and/or stimulating electrodes on the end distal from the device. The electrodes are implanted in the tissue targeted for the therapy, e.g., a particular anatomical structure of the brain.

The electrodes must be precisely implanted within the anatomical target in order to achieve a desired therapeutic effect. The increasing use and sophistication of the implantable stimulators created a need for miniature implantable leads and improved methods of introducing (implanting) the leads into the tissue.

A typical implantable Deep Brain Stimulation (DBS) lead, shown in FIG. 1A (prior art), has contacts 11 on its proximal end 12 which connects to the implantable device and sensing and/or stimulating electrodes 13 on its distal end 14 which extends from the device to an anatomical target. The lead comprises coiled conductors 15 which connect proximal contacts to the respective distal electrodes. The coiled conductors are encased in a flexible tubular insulation jacket 16. The lead is introduced into the target tissue through a cannula (guiding tube) with the aid of a stylet 17. The stylet facilitates passing the lead through the cannula and provides the required flexural stiffness when the lead emerges from the cannula. The stylet is pre-installed in the central lumen formed by the coiled conductors as shown in the enlarged breakout (FIG. 1B—prior art). The entire lead is usually iso-diametric.

A stereotactic frame (a rigid structure having markers defining a three-dimensional coordinate system—not shown) and a semi-circular arc (e.g., stereotactic arc 131, FIGS. 32A-B) are typically used to facilitate implantation of the DBS lead in the target tissue. The frame is firmly attached to the patient's head (not shown) and a calibration imaging is performed, typically using magnetic resonance imaging (MRI) or computed tomography (CT), to determine the spatial coordinates of the target tissue relative to the frame. Once this anatomical mapping is completed the stereotactic arc with appropriate instrumentation is rigidly attached to the frame. The system can be based on the center-of-arc principle wherein the center of the stereotactic arc coincides with the selected anatomical target in the brain. The use of such frame in combination with intra-operative physiological mapping of the target site and/or test stimulation enables a very precise localization (preferably within 1.0 mm) of the lead electrodes in the anatomical target in the brain.

While variations of the lead implantation procedure are practiced, the following factors are common in the art:

(A) The cannula used to guide the lead into the stimulation target is inserted into the brain. Since the diameter of the cannula is significantly larger than that of the lead, the cannula displaces significantly more brain tissue than the lead alone. This increases the risk of a brain injury or hemorrhage, especially if multiple insertion trajectories are required to achieve successful localization.

(B) Before the cannula is removed from the brain, the lead's proximal end is attached to a lead holder; otherwise the cannula would drag the lead with it due to traction on the lead. The insertion cannula is first withdrawn from the brain until the lead can be seen between the burr hole and the cannula. While manually holding the lead at the point it exits the cranium, the stylet is disengaged and removed from the lead. Still holding the lead at the exit point from the cranium, the insertion cannula and the guide tube assembly are removed. The stimulation effect is rechecked and lead placement verified. The lead is subsequently anchored in the body tissue at the exit from the burr hole.

(C) When the cannula is partially retracted to expose the lead at the exit from the burr hole, the lead's proximal contacts must still be accessible for test stimulation (i.e., not covered by the cannula). Only after the lead is securely held at the exit from the cranium and a test stimulation verifies lead dislodgement had not occurred, the lead can be detached from the lead holder and the cannula and associated lead introduction tools can be completely removed. The above constraints cause the lead to be very long, e.g., 400 mm or longer.

(D) The long lead-cannula interface generates significant traction on the lead when the cannula is being withdrawn, which can cause a lead dislodgement. When an inadvertent lead dislodgement occurs, a repositioning of the lead may be necessary, increasing the risk and expense of the procedure. A long lead also creates lead management problem since a significant lead volume must be accommodated under the scalp. Crossing lead loops can cause shorts between lead wires under prolonged pressure.

A variety of implantable stimulation leads are in use but they typically have these features:

(A) A typical lead is iso-diametric throughout its length with an outside diameter of approximately 1.3 mm.

(B) Coiled conductors are used to provide a flexible lead. However, coiled conductors are difficult to terminate (connect) to the lead electrodes in a robust manner and increase the complexity of lead construction.

(C) While coiled conductors impart flexibility, the leads with coiled conductors have a relatively poor crush resistance and are susceptible to kinking if the minimum bend radius, e.g., at the exit from a connector or from a lead anchor, is not observed.

A critical factor affecting reliability and manufacturability of the presently used leads is the termination or connection of conductors to respective electrodes and contacts. Various termination techniques have been proposed for coiled and non-coiled conductors to make these terminations more robust and easier to manufacture.

U.S. Pat. No. 6,477,427 to Stolz et al (Nov. 5, 2002) discloses a method for terminating coiled conductors to electrodes wherein the lead has a contact sleeve with a radial through-hole for receipt of the wire member and describes method of manufacture. A coil member is used that has a fixed pitch portion and a variable pitch portion. The method involves extending at least one filar member (a protruding end of wire) radially from the coil member, placing a lead body over the coil member, providing a contact sleeve over a portion of the lead body, the contact sleeve having a slot for receipt of the filar member, and welding the filar member to the contact sleeve.

U.S. Pat. No. 5,843,148 to Gijsbers et al (Dec. 9, 1998) discloses a brain stimulation lead for precise delivery of electrical stimuli to a small dense brain target, and method of positioning such lead optimally in the patient's brain. The lead has a plurality of electrodes characterized by a diagonal geometry, permitting a greater number of electrodes to be provided within a very small lineal distance, e.g. 10 mm or even 5 mm. However, the transition of coiled conductors to the electrodes is not shown and conductor-to-electrode connection is only shown diagrammatically. The patent further suggests that the use of a highly rigid stylet provides the possibility of performing stereotactic placement without the need of any additional aid such as a cannula. However the main body of the lead appears to be conventional construction with a multi-conductor coil, lumen within the coil in which is placed a stylet, and a diameter typically of about 0.13 cm.

Small anatomical brain targets, such as the subthalamic nucleus, require lead localization with a high spatial resolution and implantation procedure that minimizes micro-dislodgment of the electrodes when the lead insertion tools are being removed and when the lead is being anchored at the burr hole. Even a sub-millimeter dislodgement of the lead may result in a loss of therapy or cause undesirable side effects.

U.S. Pat. No. 6,413,263 to Lobdill et al (Jul. 2, 2002) addresses the problem of an excessive length of the lead (referred to as a probe) by disclosing "a stereotactic probe holder for maintaining a probe in position, where the stereotactic probe holder contacts the probe at a position between a stereotactic frame and a patient's head, and where the stereotactic probe holder comprises an adjustable support, a locking means effective to substantially immobilize the stereotactic probe holder, and a gripping means, attached to the adjustable support, that is effective to hold the probe."

However, the probe holder can immobilize the lead only after the brain cannula is retracted to expose the lead, which refraction may in itself be a cause of lead dislodgement. In addition, the probe holder is yet another tool to be attached to a stereotactic system which increases setup complexity and may undesirably obscure access to the burr hole site.

Therefore, lead systems and lead introduction methods to eliminate or minimize dislodgement of the DBS are desirable, preferably using the native stereotactic introduction tools, i.e., without additional devices attachable to the stereotactic frame. Removal of the lead introduction tools without manual intervention (manually holding the lead) is also desired.

One advantage of coiled conductors is their flexibility and resistance to a flexing fatigue. This is especially critical if the lead is placed in an articulated part of the body and/or is passing through a mobile tissue, e.g., passing through the neck. While brain tissue and under-the-scalp environment are essentially immobile, coiled wire conductors are nonetheless common in DBS leads due to their flexibility and amenability to receiving a stylet in the coil's lumen. Another important requirement for a DBS lead is the crush resistance, since the lead may be routed over cranium irregularities, and may be crossing itself. However, the crush resistance is rather poor in the leads utilizing coiled conductors.

The process of arriving at the final and efficacious lead position in the target may involve multiple incremental steps, employing recording of cell activities and test stimulation. If lead localization is not successful, it may be necessary to adjust the stereotactic coordinates and attempt a different trajectory. If a lead localization is successful but a lead dislodgement occurs (e.g., due to removal of lead introduction tools) it may be necessary to repeat introduction of the lead along the same trajectory. Robust leads and introduction tools are therefore needed that could withstand multiple introduction cycles.

The wiring of the present leads cannot be fully optimized due to limitations of traditional iso-diametric construction based on coiled conductors, and the interdependence of this construction and introduction tools. For example, entire lead must accommodate a stylet and the lead must be sufficiently long to allow holding of the lead at the proximal end until the cannula is retracted from the brain to allow holding of the lead at the exit from the burr hole.

U.S. Pat. No. 7,454,251 to Rezai et al (Nov. 18, 2008) lists numerous issues caused by an excessive lead length (susceptibility to electromagnetic radiation or "antenna effect", MRI safety, random management of excess lead, difficulty in making revision surgery, etc.) and discloses a device and method for retaining an excess portion of the implanted lead.

SUMMARY

In one or more aspects the present implantable medical leads and systems address the need for improved leads for use with implantable devices, such as a neurostimulator. A lead construction allows a distal electrode terminal and a connecting cable to be optimized independently from a stylet assembly. The cable connecting distal electrodes to proximal contacts can be shorter since the requirement for immobilizing the lead by attaching the lead's proximal end to the stereotactic instrument is removed. The length of the lead is not dictated by the requirement that the proximal end of the lead is immobilized when the cannula is removed. A variety of conductor and cable constructions can be used to provide flexibility and high crush resistance.

A method of terminating conductors to electrodes using inserts is employed which is suitable for very fine wires and particularly advantageous for stranded conductors. Multiple insert configurations are described.

Another aspect uses lead introduction tools based on an external stylet. The use of a brain-entering cannula can be eliminated; a relatively stiff external stylet provides the requisite stiffness and thus allows the cannula to remain completely out of the brain.

A reinforced electrode terminal can be coupled with the external stylet in a manner that reduces flexing and tilting of the distal end of the lead. The reinforcing also facilitates robust small-dimensioned electrode terminals that are resistant to bending and buckling and are therefore suitable for repeated lead introductions.

The stylet assembly comprising a stylet and a stylet spacer allows removal of the stylet and the cannula without causing the lead to retract. The stylet constrains the lead from retracting when the stylet spacer is being removed and when the cannula is being retracted. Once the stylet spacer is removed the stylet can be lifted with the remaining insertion tools without generating traction on the lead. A lead dislodgement due to the disassembly of the introduction tools is thus minimized.

Lead introduction tools allow introduction of leads with minimal direct manual handling of the lead. In some embodiments the lead can be anchored at the burr hole while an immobilized stylet holds the lead from retracting.

DRAWINGS

FIG. 1A is a perspective view of an iso-diametric lead of the prior art, with a stylet installed.

FIG. 1B is a magnified breakout of FIG. 1A showing coiled conductors and the internally disposed stylet.

FIG. 2 is a perspective view of an embodiment of a lead having a stepped body portion with a shoulder adapted for use with an external stylet assembly, shown side-by-side with the stylet assembly.

FIG. 3A-D are variations of a cross-sectional view of the lead of FIG. 2, taken at the cable, as indicated by the lines 3-3 of FIG. 2.

Figure 4:
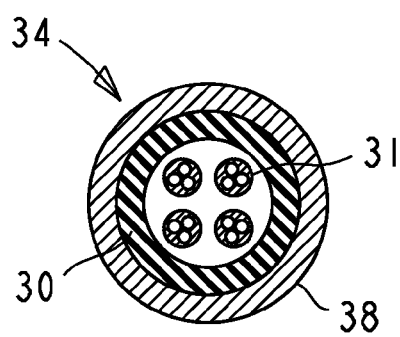
Figure 4:
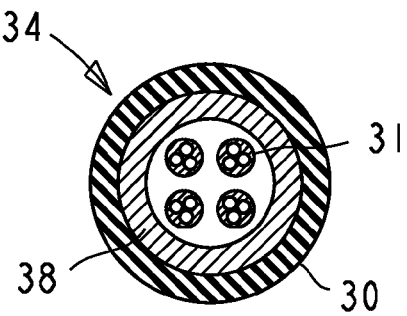

FIG. 4A-B are variations of a cross-sectional view of the lead of FIG. 2, taken at the reinforced portion of the cable, as indicated by the lines 4-4 of FIG. 2.

FIG. 5A is a side view of the lead of FIG. 2 with the stylet assembly installed.

FIG. 5B is an enlarged view of FIG. 5A with the stylet and stylet spacer shown in cross-section.

FIG. 6A is a partial side view of a lead-stylet assembly employing a spring retention mechanism, shown with the stylet partially assembled.

FIG. 6B is a partial side view of a lead-stylet assembly employing a spring retention mechanism, shown with the stylet fully assembled.

Figure 7:
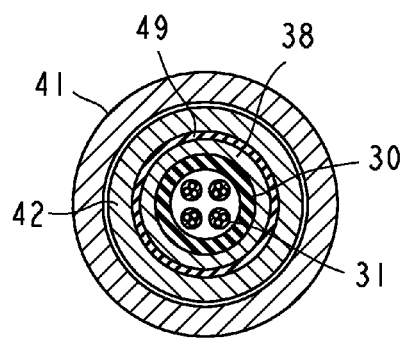

FIG. 7 is a cross-sectional view of the lead-stylet assembly of FIG. 5B, taken as indicated by the lines 7-7 of FIG. 5B.

Figure 8:
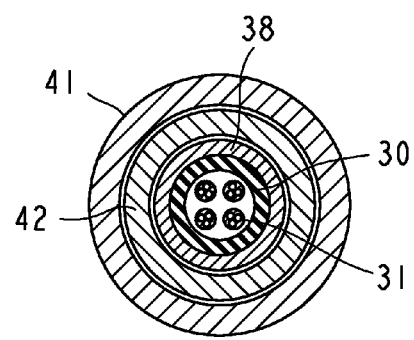

FIG. 8 is a cross-sectional view of the lead-stylet assembly of FIG. 5B, taken as indicated by the lines 8-8 of FIG. 5B.

Figure 9:
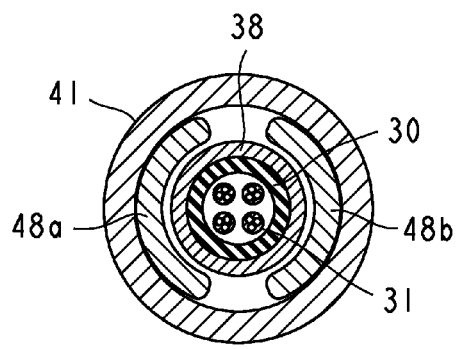

FIG. 9 is a cross-sectional view of the lead-stylet assembly of FIG. 6B, taken as indicated by the lines 9-9 of FIG. 6B.

Figure 10:
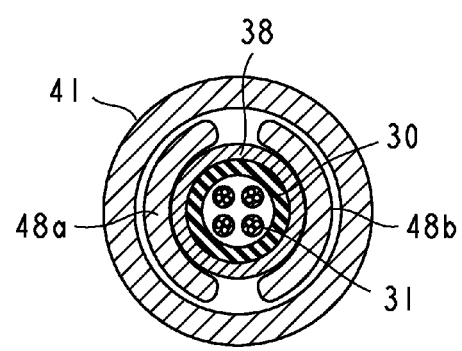

FIG. 10 is a cross-sectional view of the lead-stylet assembly of FIG. 6B, taken as indicated by the lines 10-10 of FIG. 6B.

Figure 11:
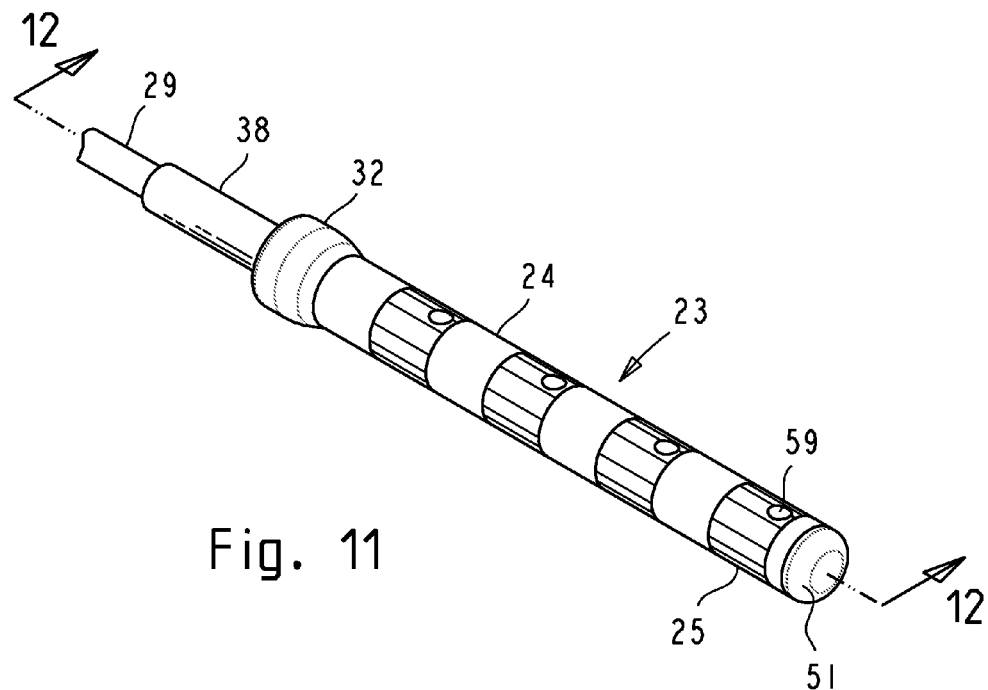

FIG. 11 is a partial perspective view of the distal portion of the lead of FIG. 2.

Figure 12:
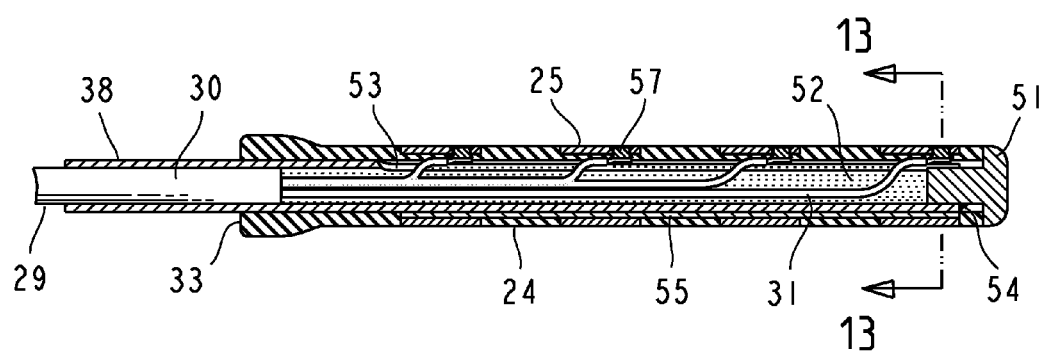

FIG. 12 is a longitudinal cross-sectional view of the lead portion of FIG. 11, taken axially, as indicated by the lines 12-12 of FIG. 11.

Figure 13:
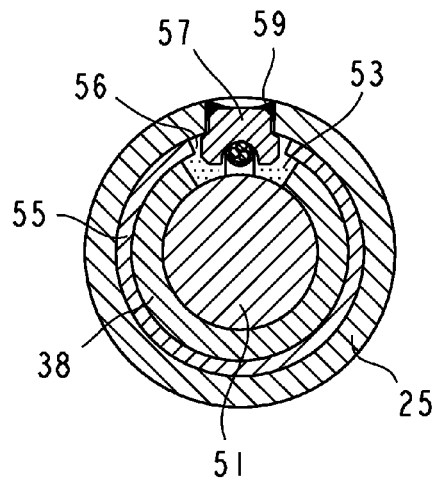

FIG. 13 is a magnified cross-sectional view of the electrode terminal of FIG. 11, taken as indicated by the lines 13-13 of FIG. 12.

FIGS. 14A-B are detail views of a conductor terminated to the insert of FIG. 13.

Figure 14:
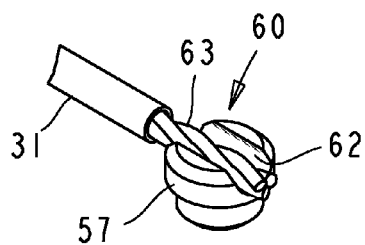
Figure 14:
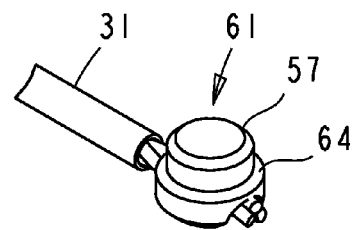
Figure 15:
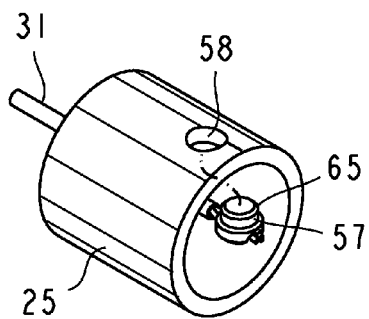

FIG. 15 is a perspective view of a conductor-insert assembly of FIGS. 14A-B, shown with an electrode.

Figure 16:
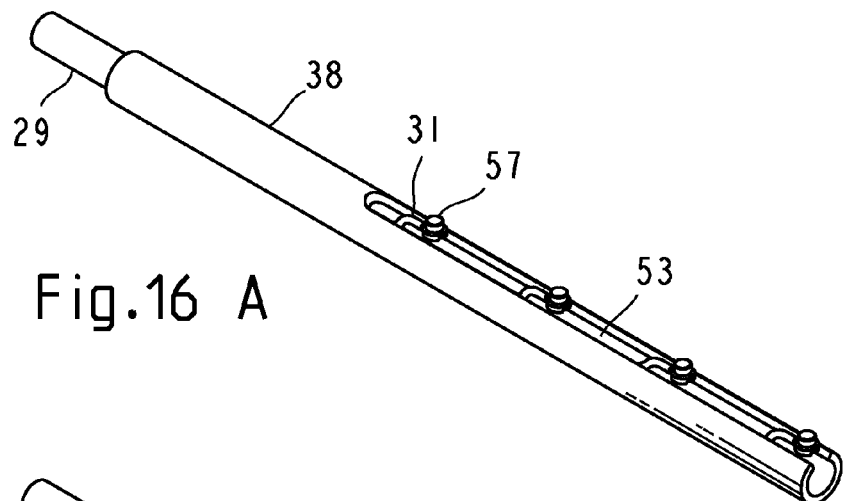
Figure 16:
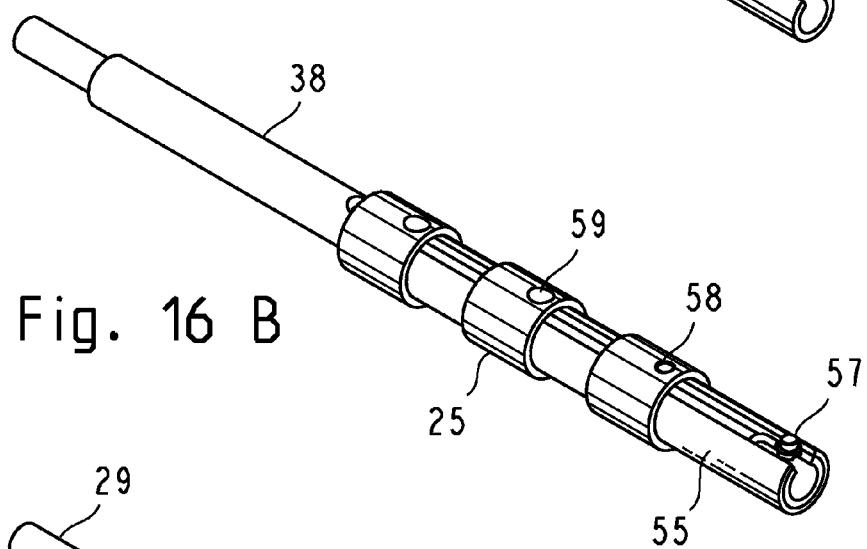
Figure 16:
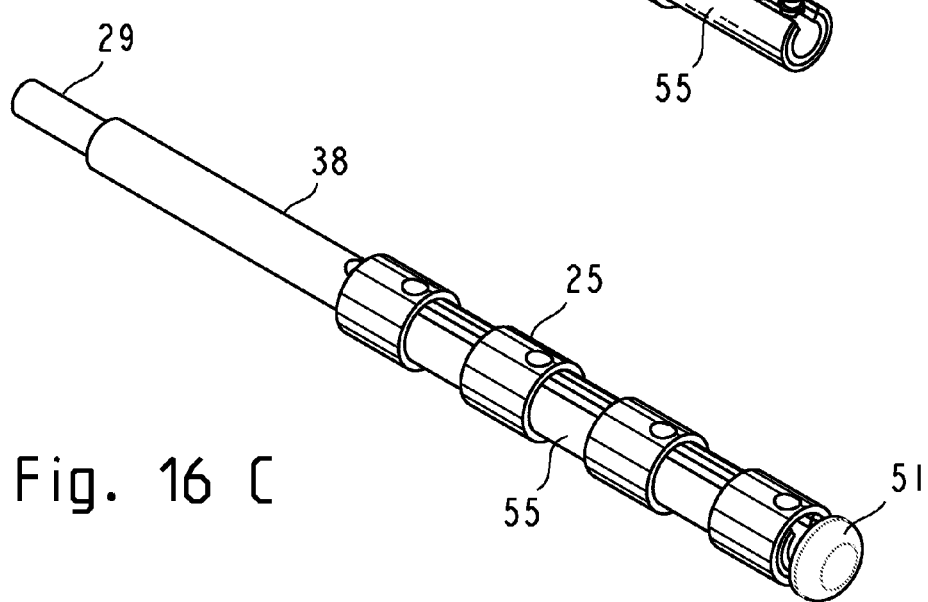

FIG. 16A-C show three stages of assembly of the electrode terminal of FIG. 11.

FIG. 17A is a perspective view of an embodiment of a lead having a sheath adapted to accommodate a stylet spacer.

FIG. 17B is an enlarged partial cross-sectional view of the lead of FIG. 17A with a stylet and a stylet spacer installed.

Figure 18:
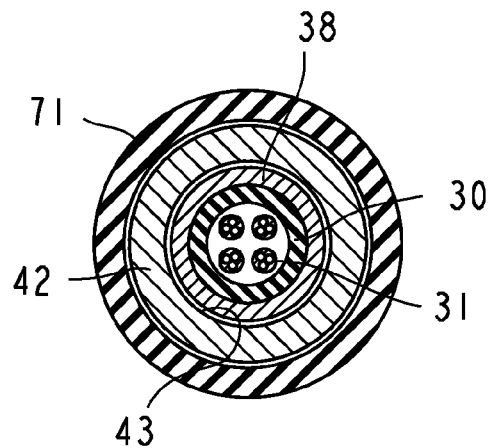

FIG. 18 is a cross-sectional view of the lead-stylet assembly of FIG. 17B, taken as indicated by the lines 18-18 of FIG. 17B.

Figure 19:
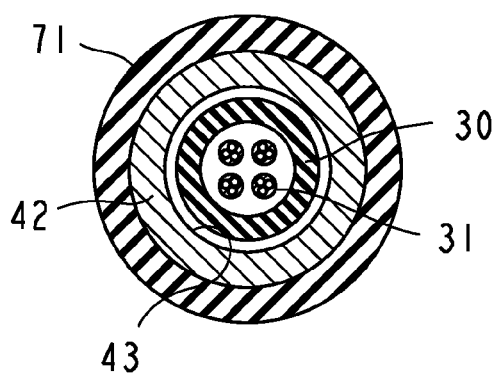

FIG. 19 is a cross-sectional view of the lead-stylet assembly of FIG. 17B, taken at the sheath, as indicated by the lines 19-19 of FIG. 17B.

Figure 20:
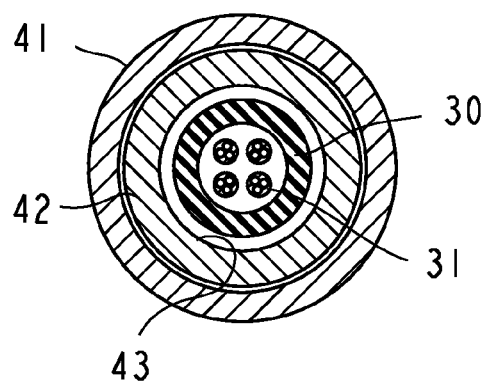

FIG. 20 is a cross-sectional view of the lead-stylet assembly of FIG. 17B, taken at the sheath, as indicated by the lines 20-20 of FIG. 17B.

Figure 21:
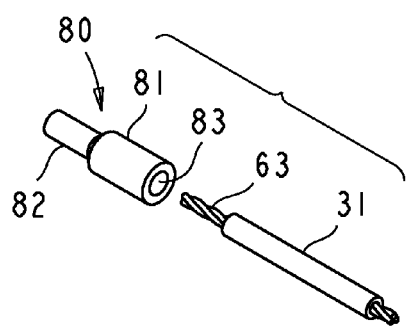

FIG. 21 shows an embodiment of a tubular insert and a conductor end portion before termination.

Figure 22:
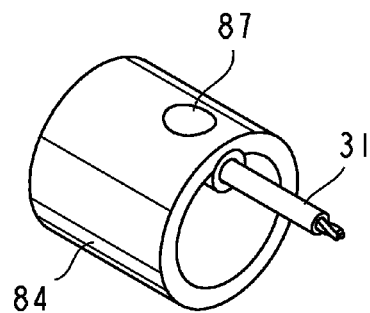

FIG. 22 shows a terminated insert-conductor pair of FIG. 21, attached to an electrode.

Figure 23:
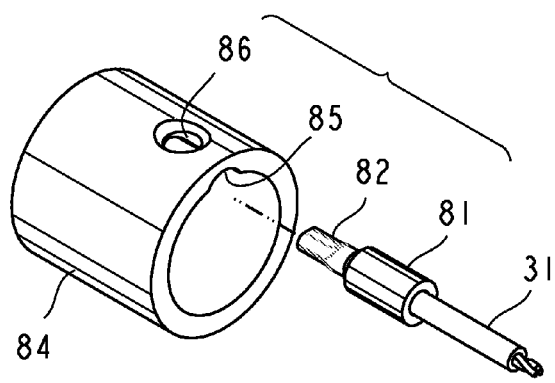

FIG. 23 shows a crimped insert-conductor pair being assembled with an electrode.

Figure 24:
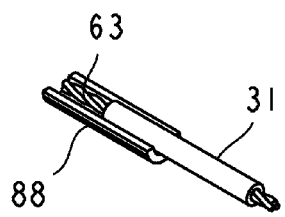

FIG. 24 shows a half-tubular insert with a corresponding conductor portion.

Figure 25:
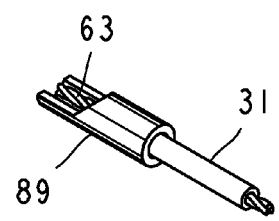

FIG. 25 shows another variation of a tubular insert with a corresponding conductor portion.

FIGS. 26A and 26B are magnified detail views of an embodiment of a conductor-insert-electrode assembly utilizing an arcuate insert attached at the electrode's cross-hole.

FIGS. 27A and 27B are magnified detail views of an embodiment of a conductor-insert-electrode assembly utilizing an arcuate insert attached to the electrode's edge.

FIGS. 28A-C are detail views of an embodiment of a conductor-insert-electrode assembly utilizing an insert that is co-planar with the outer surface of the electrode after attachment.

FIG. 29 is a detail view of a variation of the conductor-insert-electrode assembly of FIG. 28B.

FIG. 30 shows a conductor terminated directly to the inner surface of an electrode.

Figure 31:
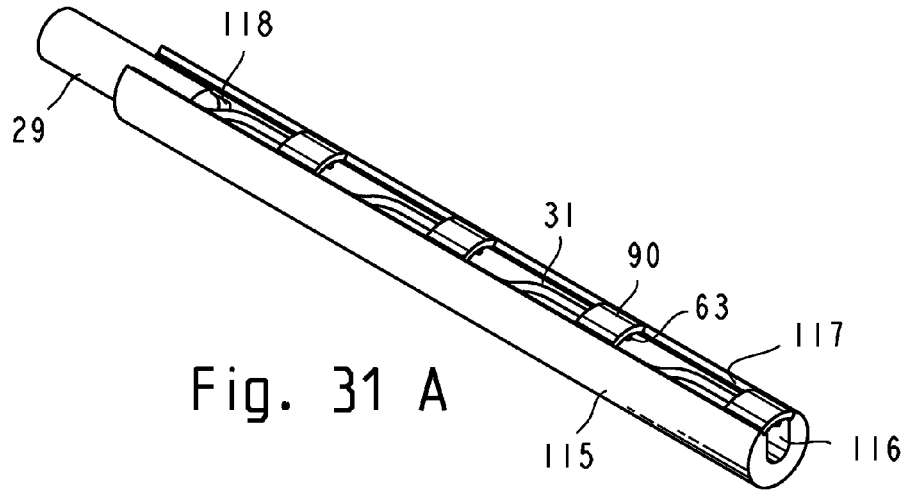
Figure 31:
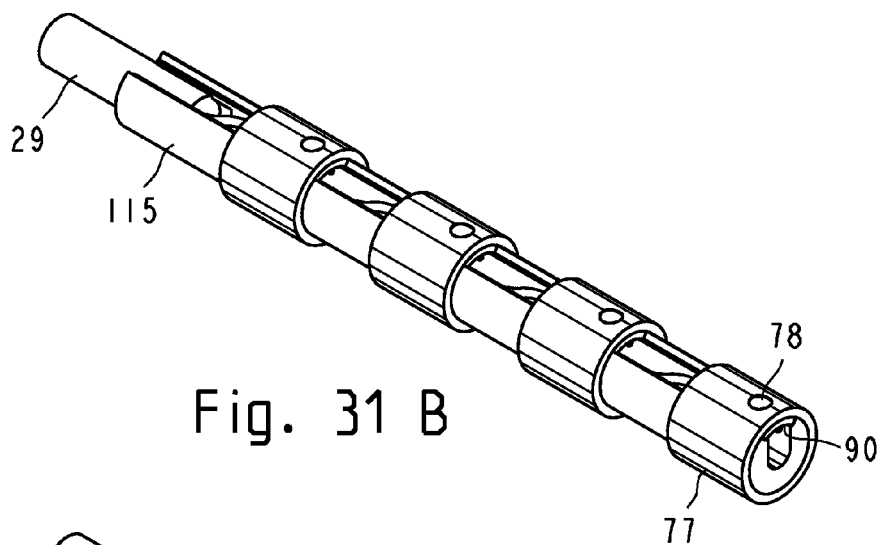
Figure 31:
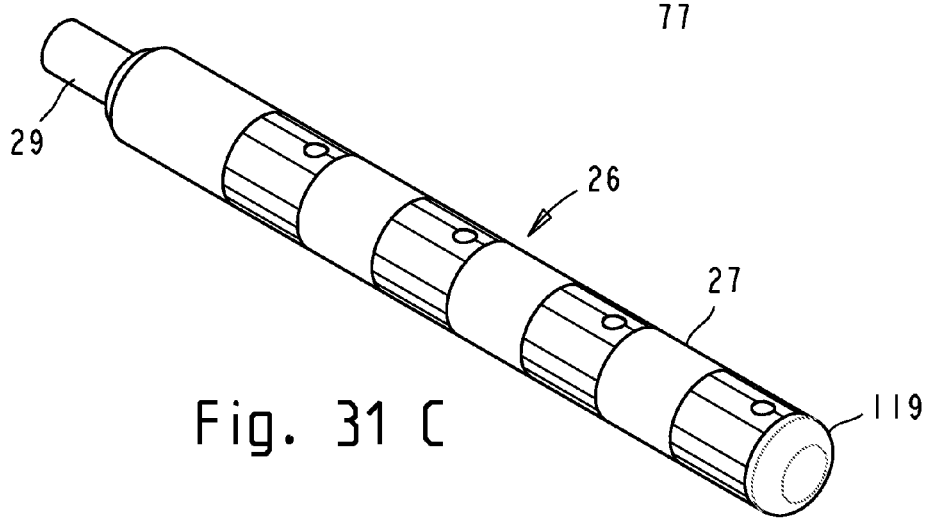

FIGS. 31A-C show three stages of a connector terminal assembly.

Figure 32:
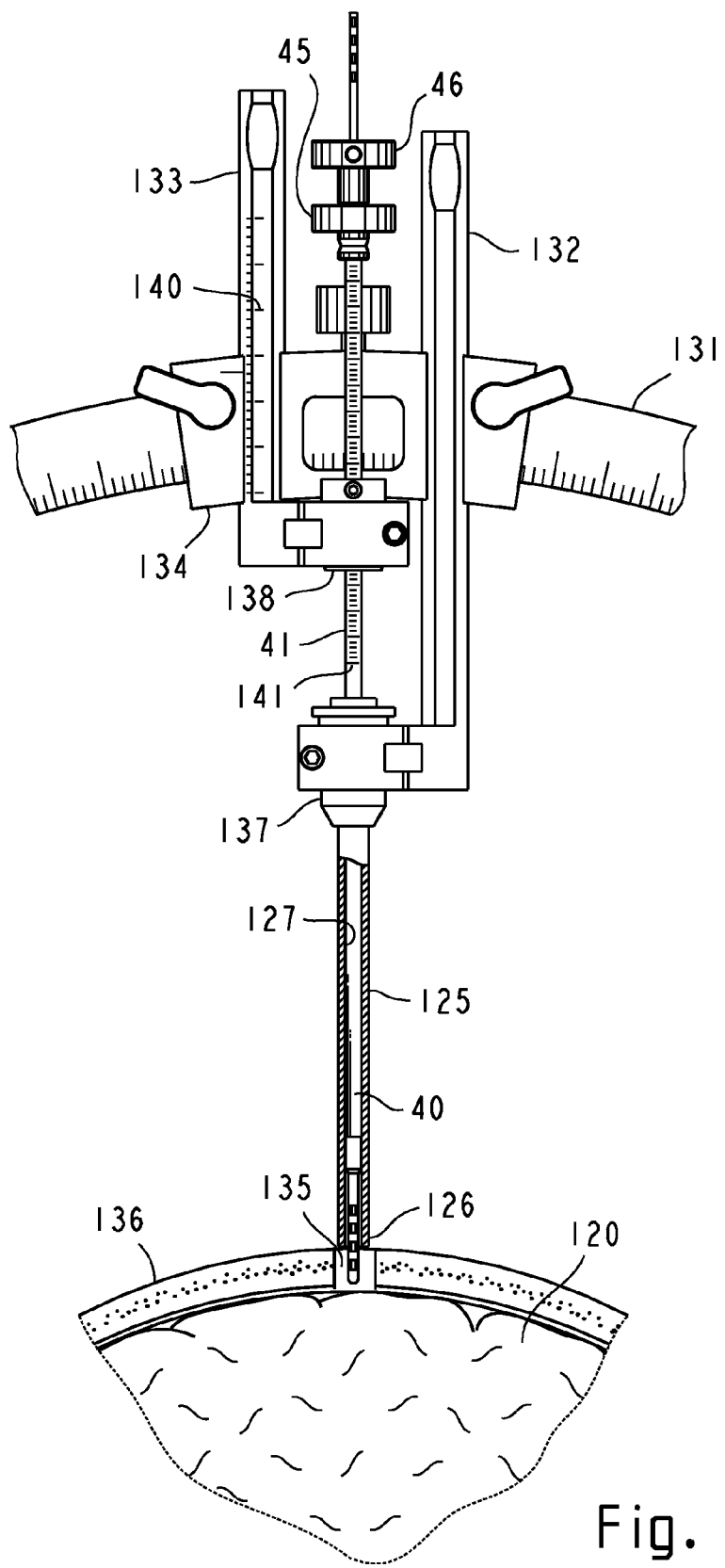
Figure 32:
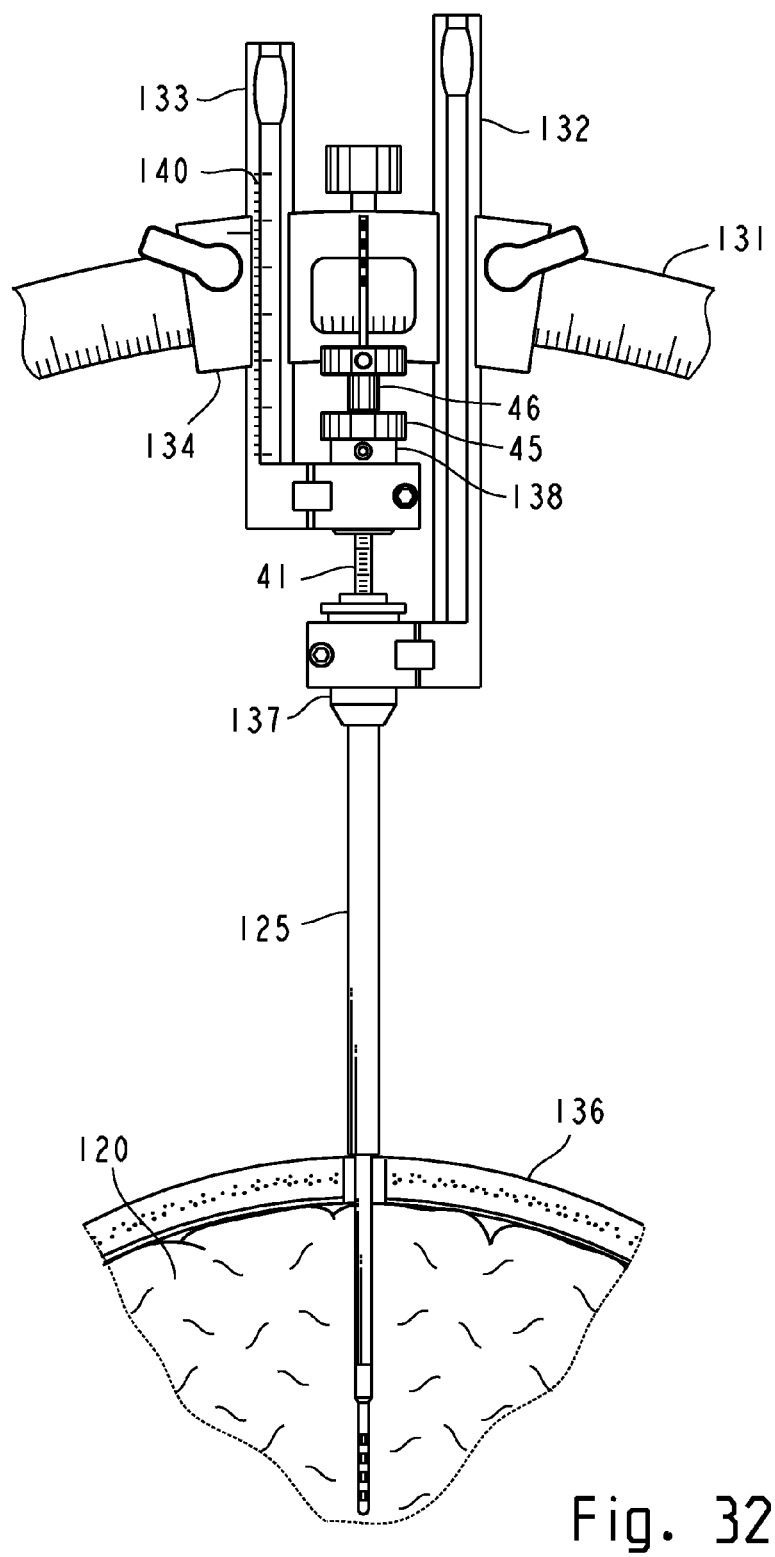

FIGS. 32A-B show a lead introduction system utilizing a stereotactic frame for introducing a lead with external stylet assembly.

FIGS. 33A-B are partial cross-sectional views of FIG. 32A-B showing lead introduction tools in greater detail.

Figure 34:
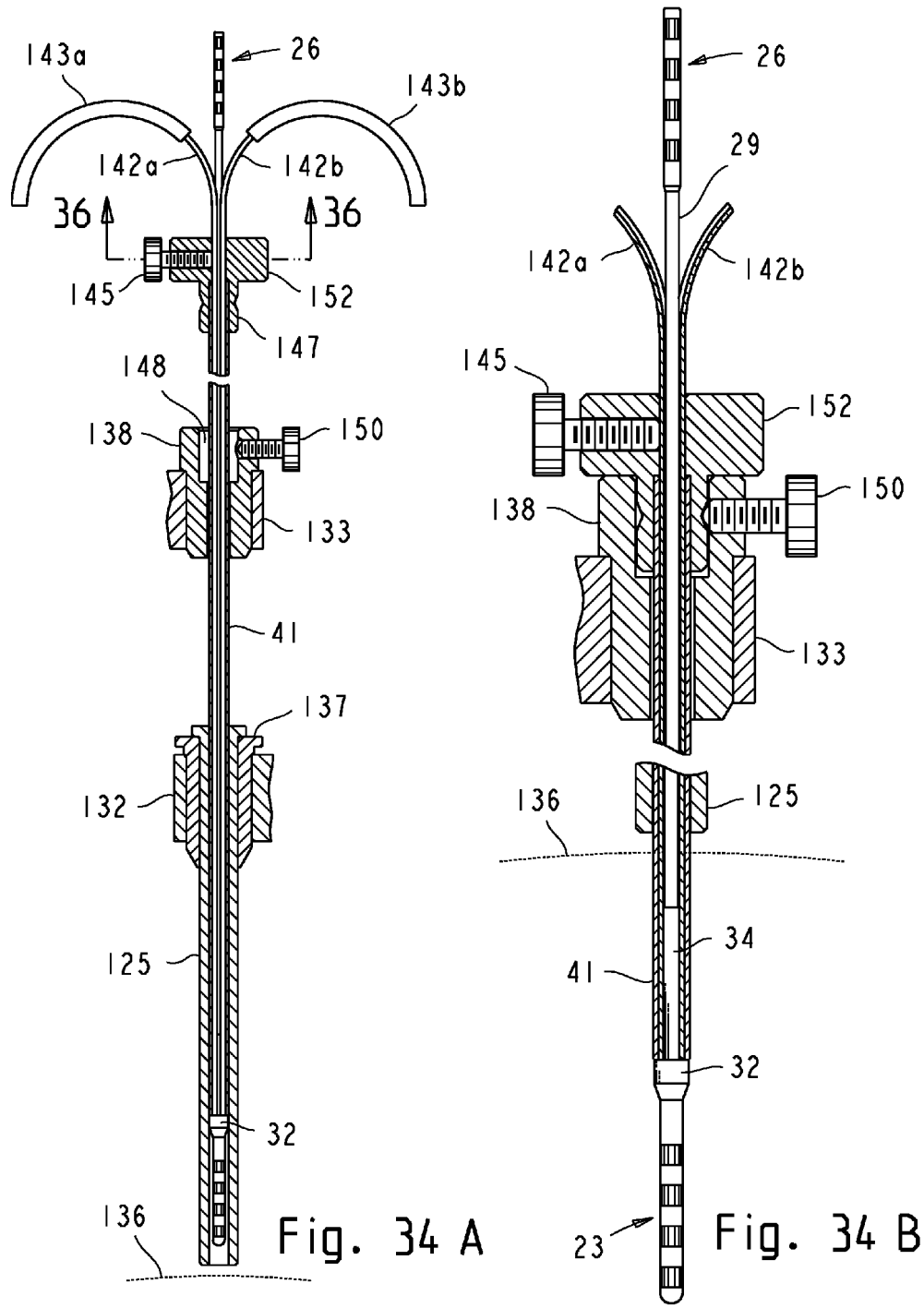

FIG. 34A-B are partial cross-sectional views of the lead introduction tools adapted for introducing a lead with a stylet spacer comprising two segments.

FIG. 35A is a cross-sectional view of a coupling mechanism between a stylet spacer's handle and a lead's cable, taken as indicated by the lines 35-35 of FIG. 33A.

FIG. 35B is a cross-sectional view of a quick release coupling mechanism between a stylet spacer's handle and a lead's cable, taken as indicated by the lines 35-35 of FIG. 33A.

Figure 36:
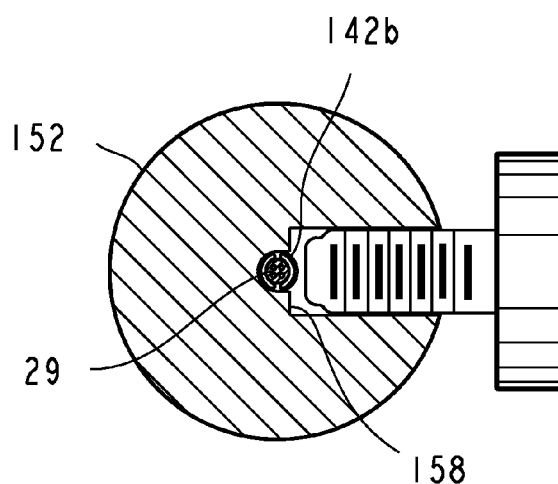

FIG. 36 is a cross-sectional view of a coupling mechanism between a stylet's handle and a lead's cable, taken as indicated by the lines 36-36 of FIG. 34A.

FIGS. 37A-B are perspective views of a lead-stylet assembly with a screw-driven mechanism for disengaging a stylet spacer from a lead.

FIGS. 38A-B are partial cross-sectional views of lead introduction system utilizing the screw-driven spacer disengagement mechanism of FIG. 37A.

Figure 39:
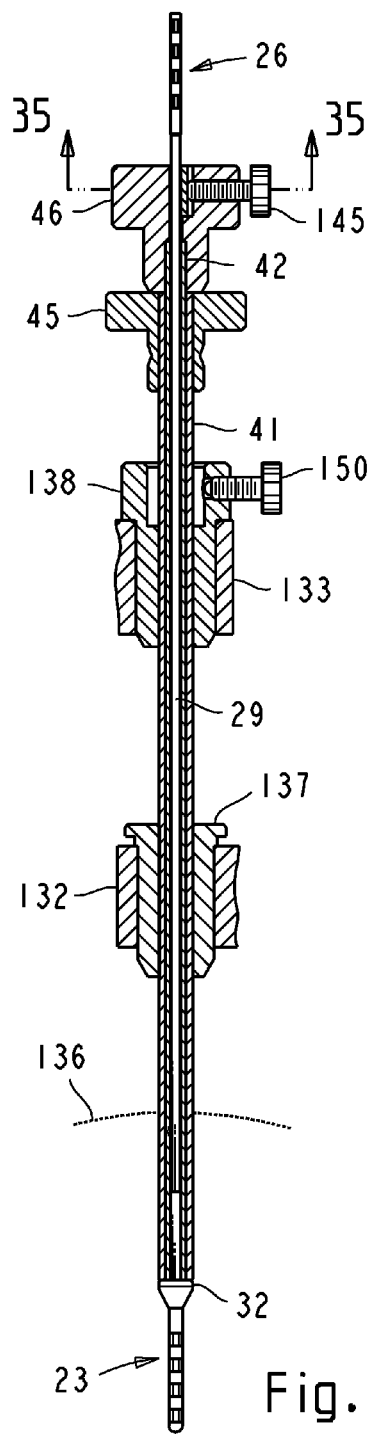

FIG. 39 is a partial cross-sectional view of a lead introduction system equivalent to that in FIG. 33A, with the cannula eliminated and the cannula guide bushing adapted to slidably guide the stylet.

FIGS. 40A-D are partial cross-sectional views of a lead introduction system which does not utilize a cannula and has a single stop/guide bushing.

Figure 41:
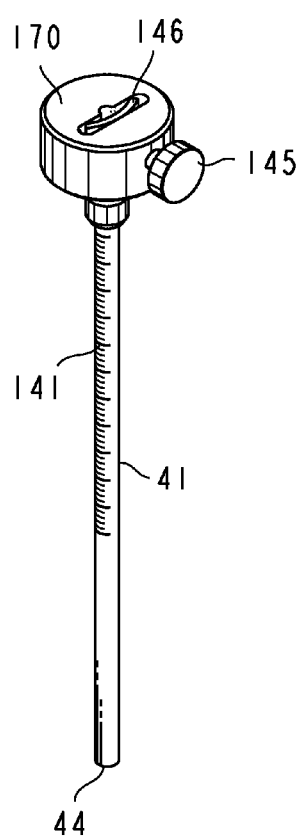

FIG. 41 is perspective view of an external stylet assembly for use with a brain-entering cannula.

Figure 42:
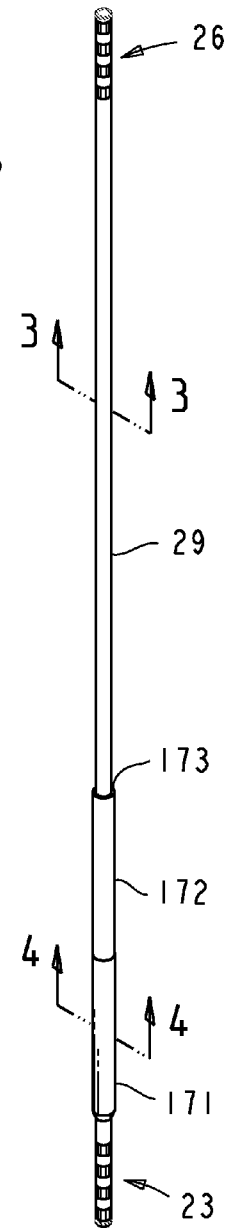

FIG. 42 is a perspective view of a lead designed for use with an external stylet and a brain-entering cannula.

Figure 43:
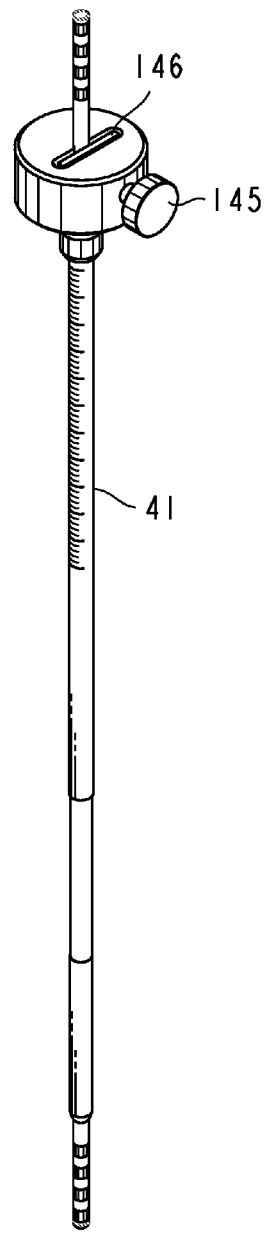

FIG. 43 is a perspective view of a lead-stylet assembly for use with a brain-entering cannula.

Figure 44:
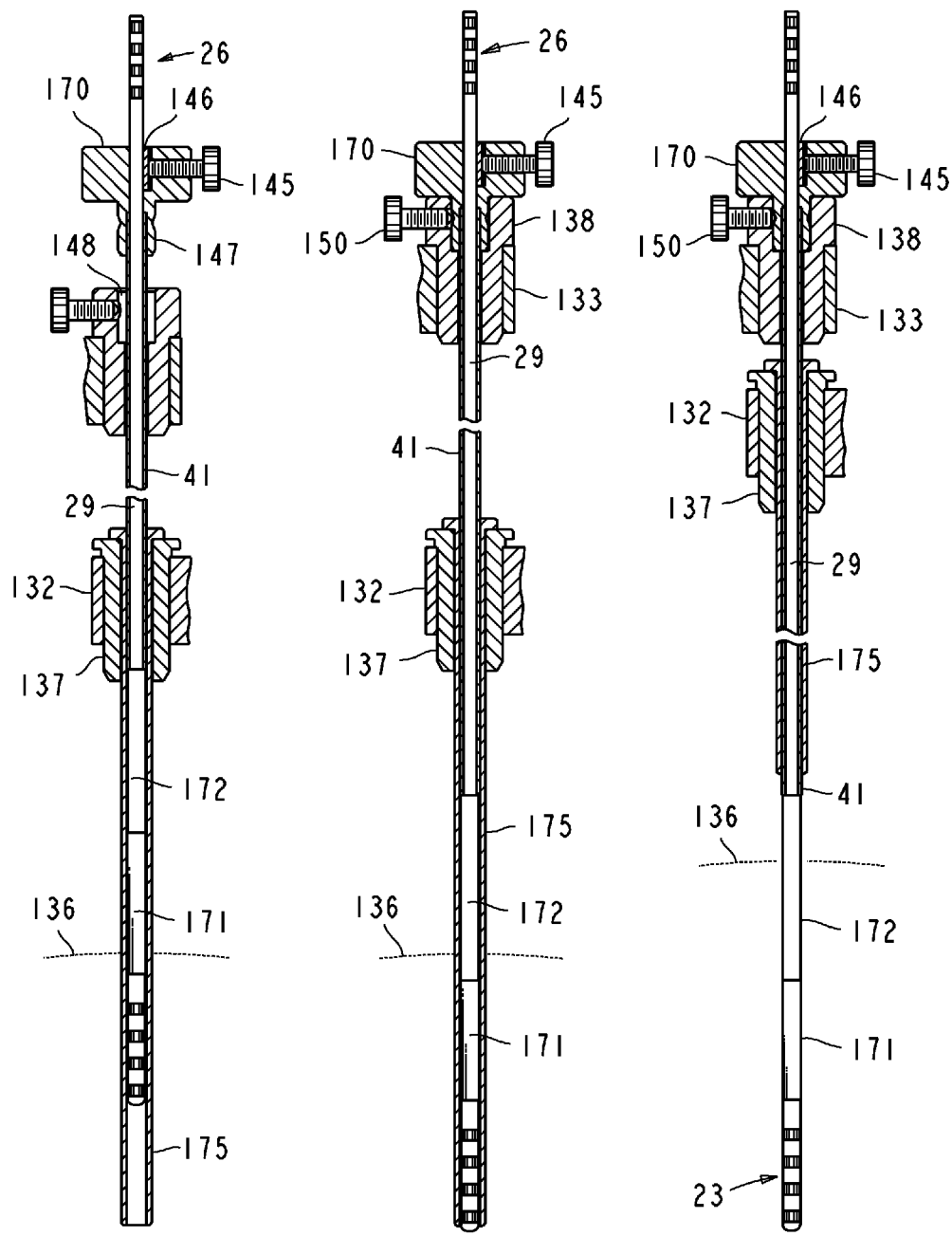

FIGS. 44A-C are partial cross-sectional views of a lead introduction system utilizing a cannula that is pre-inserted into the brain and an external stylet adapted to immobilize the lead during cannula removal and lead anchoring.

FIGS. 45A-C are partial cross-sectional views of a lead introduction system for a lead with an internal stylet, adapted to immobilize the lead during cannula removal and lead anchoring.

FIGS. 46A-B are partial cross-sectional views of a lead introduction system for a lead with an internal stylet, adapted to immobilize the lead during cannula removal and lead anchoring, further comprising an external connector for connecting the lead to an external pulse generator.

Figure 47A:
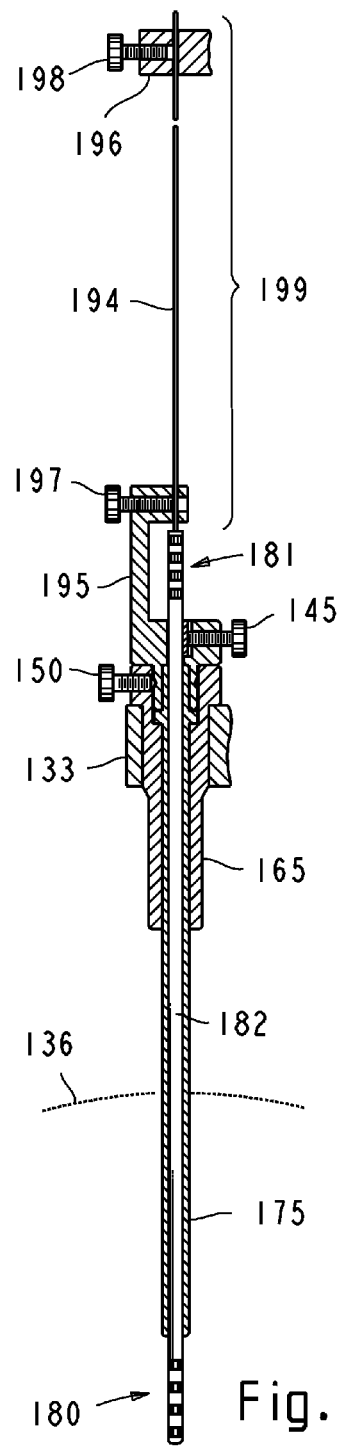
Figure 47B:
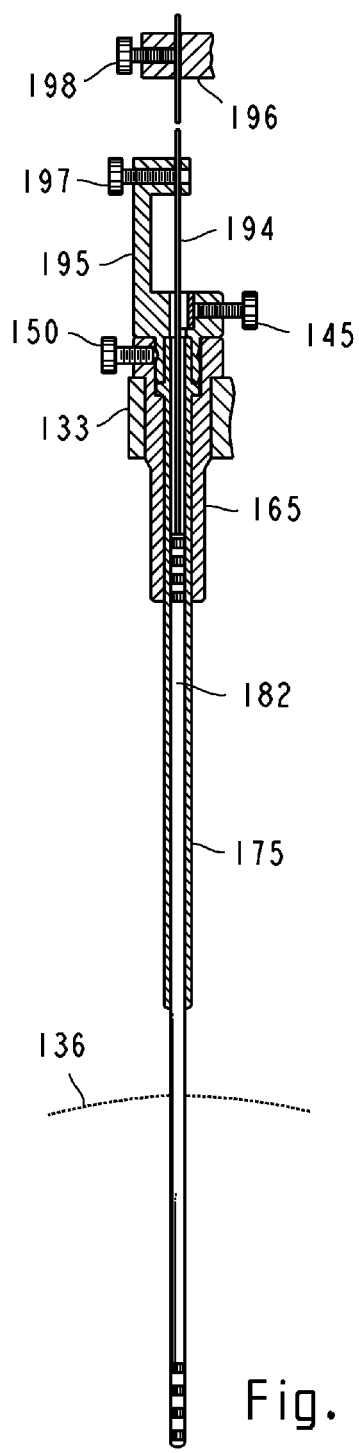

FIGS. 47A-B are partial cross-sectional views of a lead introduction system for a lead with an internal stylet, utilizing a cannula that can be coupled to the stylet assembly.

| DRAWINGS - Reference Numerals | |
|---|---|
| 11 | contact (prior art) |
| 12 | proximal end (prior art) |
| 13 | electrode (prior art) |
| 14 | distal end (prior art) |
| 15 | conductors, coiled (prior art) |
| 16 | jacket, insulating (prior art) |
| 17 | stylet (prior art) |
| 20 | lead |
| 21 | proximal end |
| 22 | distal end |
| 23 | electrode terminal |
| 24 | body, electrode terminal |
| 25 | electrode |
| 26 | connector terminal |
| 27 | body, connector terminal |
| 28 | contact |
| 29 | cable |
| 30 | jacket, insulating |
| 31 | conductor |
| 32 | stepped portion, lead |
| 33 | shoulder, lead |
| 34 | cable portion, reinforced |
| 35 | body, insulating |
| 36 | body, insulating |
| 37 | core, elastomeric |
| 38 | tube, reinforcing |
| 39 | opening, stylet assembly |
| 40 | stylet assembly |
| 41 | stylet |
| 42 | spacer, stylet |
| 43 | lumen, stylet |
| 44 | distal end, stylet sleeve |
| 45 | handle, stylet |
| 46 | handle, stylet spacer |
| 47 | stylet spacer, bifurcated |
| 48 | end portion, spacer |
| 49 | adhesive, shearable |
| 50 | bow, stylet segment |
| 51 | tip, distal |
| 52 | potting, electrode terminal |
| 53 | slot, reinforcing tube |
| 54 | joint, tip |
| 55 | interliner sleeve |
| 56 | opening, interliner |
| 57 | insert |
| 58 | cross hole |
| 59 | weld |
| 60 | termination side, insert |
| 61 | weld side, insert |
| 62 | slot, insert |
| 63 | bare end, conductor |
| 64 | shoulder, insert |
| 65 | chamfer |
| 70 | lead |
| 71 | sheath |
| 72 | opening, sheath |
| 73 | outer end, sheath |
| 77 | electrode |
| 78 | cross hole, weld |
| 79 | electrode |
| 80 | insert, tubular |
| 81 | insert body, tubular |
| 82 | necked portion, insert |
| 83 | hole, insert |
| 84 | electrode |
| 85 | arcuate cutout, electrode |
| 86 | cross hole |
| 87 | weld |

-continued

| DRAWINGS - Reference Numerals | |
|---|---|
| 88 | insert, arcuate |
| 89 | insert, partly tubular |
| 90 | insert, arcuate |
| 91 | inner surface, insert |
| 92 | outer surface, insert |
| 93 | front edge, insert |
| 94 | back edge, insert |
| 95 | bared end, conductor |
| 96 | recessed surface, electrode |
| 97 | step, electrode |
| 98 | rim, electrode |
| 99 | weld line |
| 101 | insert |
| 102 | cutout, electrode |
| 103 | electrode |
| 104 | inner surface, insert |
| 105 | outer surface, insert |
| 106 | back edge, insert |
| 107 | edge, insert |
| 108 | weld line |
| 109 | rim edge, electrode |
| 110 | insert, slotted |
| 111 | slotted portion, insert |
| 112 | inner surface, electrode |
| 113 | electrode |
| 115 | core |
| 116 | channel |
| 117 | rail, core |
| 118 | distal portion, channel |
| 119 | tip, proximal |
| 120 | brain |
| 125 | cannula |
| 126 | distal end, cannula |
| 127 | central lumen, cannula |
| 131 | stereotactic arc |
| 132 | guide holder |
| 133 | stop holder |
| 134 | instrument carrier |
| 135 | burr hole |
| 136 | cranium |
| 137 | guide, cannula |
| 138 | bushing, stop |
| 140 | scale, sliding arm |
| 141 | marks, stylet |
| 142 | spacer segment |
| 143 | handle, spacer segment |
| 145 | screw, handle |
| 146 | interposer, spring |
| 147 | neck, handle |
| 148 | counterbore, stop bushing |
| 149 | notch |
| 150 | screw, stop bushing |
| 151 | plunger |
| 152 | handle, stylet |
| 153 | body, spring loaded button |
| 154 | spring |
| 155 | resilient lining |
| 156 | handle |
| 157 | back portion, body |
| 158 | bottom, threaded hole |
| 160 | handle, stylet |
| 161 | handle, stylet spacer |
| 162 | nut, driving |
| 163 | key, guiding |
| 164 | hole, guide |
| 165 | stop/guide bushing |
| 168 | radial clearance |
| 170 | handle, stylet |
| 171 | reinforced portion, cable |
| 172 | thickened portion, cable |
| 173 | shoulder, cable |
| 175 | cannula, brain |
| 180 | electrode terminal |
| 181 | connector terminal |
| 182 | cable |
| 183 | stylette |
| 184 | lumen, lead |

-continued

| DRAWINGS - Reference Numerals | |
|---|---|
| 185 | stylet, internal |
| 186 | handle, stylet |
| 187 | cable portion |
| 188 | connector, external unit |
| 189 | contact, resilient |
| 190 | handle, stylet |
| 191 | contact, lead |
| 194 | stylet |
| 195 | handle, stylet |
| 196 | stylet holder |
| 197 | screw, handle |
| 198 | screw, stylet holder |
| 199 | stylet, proximal extension |

DETAILED DESCRIPTION

Glossary

In the ensuing description and claims, the following terms have the meanings indicated.

"Lead" encompasses a stimulation lead, a sensing lead, or a combination thereof, intended for a chronic implantation.

"Stylet assembly" encompasses stylets and accessories such as stylet spacers and handles, providing the requisite stiffness to the lead, and travelling with the lead, when the lead is advanced into the tissue.

"Lead introduction" refers to the procedure of implanting the lead, including use of temporary electrode probes for physiological mapping of the target site and test stimulation required to verify electrode localization and to confirm a desired therapeutic effect.

"Introduction tools" refers to the surgical tools, adapters, and accessories used to accomplish the lead introduction procedure.

"Insertion trajectory" refers to a straight path through the tissue to the intended target, as defined by lead introduction tools.

"Anatomical target" refers to the ideal or optimal location for lead electrode implantation, as determined by imaging and/or physiological mapping.

"Proximal" and "distal" (near and distant) are used with reference to a device or an external instrument. I.e., "proximal" means proximal to the device and "distal" means distal from the device. Similarly, a proximal direction is the direction toward a device and a distal direction is the direction away from the device and toward the target tissue.

"Deep brain stimulation" or "DBS" refers to a treatment involving a surgically implanted medical device and lead(s) which deliver electrical stimuli to a specific anatomical target in the brain.

FIG. 2—Lead with Stepped Body

Traditional iso-diametric leads are designed to be passable through a cannula so that the cannula can be removed by sliding it over the lead after the lead is successfully localized in the target tissue. An iso-diametric lead typically has coiled conductors with a stylet accommodated within the central lumen (inside diameter) of the coiled conductors. The stylet is relatively thin (approx. 0.4 mm diameter) and relies on a brain-entering cannula to provide additional stiffness necessary to maintain the stylet's pointing accuracy. The lead can be very long (400 mm or more) to satisfy the requirements of the introduction tools, as discussed in the prior art section above. The iso-diametric lead construction is thus in large measure constrained by the use of coiled conductors and by the requirements of the associated lead introduction tools and methods.

The disclosed leads and the associated introduction tools and methods remove the traditional constraints on the lead cable construction. In particular, an external stylet assembly allows the cable portion of the lead to be lumen-free. Cable construction can thus be optimized for a particular need.

FIG. 2 is a perspective view of an embodiment of a variable section (non-iso-diametric) lead 20 shown side by side with a cooperating stylet assembly 40. The lead has a proximal end 21 and a distal end 22, and an elongated body with a stepped outside diameter. The lead comprises an electrode terminal 23 having a body 24 and at least one electrode 25 at the distal end of the lead, a connector terminal 26 having a body 27 and at least one contact 28 at the proximal end of the lead, and a conductor cable 29 having an insulating jacket 30 and at least one conductor 31 (FIGS. 3A-D) electrically connecting at least one electrode to at least one contact.

The lead further comprises a stepped body portion 32 which has a larger outside diameter than the cable body, forming a proximally facing annular surface or shoulder 33. The shoulder provides a stop and a bearing surface for the stylet assembly. A distal portion 34 of the cable is stiffened with a reinforcing means and designed to be coaxially received in the stylet assembly 40.

The stepped portion is preferably contiguous or integrally formed with the electrode terminal body. The outside diameter of the electrode terminal can be significantly smaller than the outside diameter of the stepped portion, e.g., to optimize the electrodes for small anatomical targets. In such case, the stepped portion also forms a collar that helps to stabilize or anchor the electrode terminal in the target tissue. Alternatively, the electrode terminal and the stepped portion can have substantially equal diameters.

The electrode terminal, the stepped portion, the reinforced portion of the cable body, and at least a portion of the cable are designed for introduction into the brain. The combined length of the electrode terminal, the stepped portion, and the reinforced portion of the cable body is therefore smaller than the maximum depth of any of the contemplated anatomical targets in the brain. The remaining portion of the lead is implanted under the scalp and routed to the implantable device (e.g., a neurostimulator) where the connector terminal is disengageably electrically connected to the device's feedthrough connector.

The outside surface of the electrode terminal is preferably circular, but can be of any shape that forms a smooth outside surface. The smooth surface minimizes traction when passing through the tissue or through a cannula and mitigates an adverse long term tissue reaction.

Stylet assembly 40, shown separated from the lead, comprises a stylet 41 and a stylet spacer 42. The stylet is the outer member of the stylet assembly which facilitates passing of the lead through a cannula (or similar guiding tool) and provides the requisite stiffness for introducing the lead into the target tissue. The stylet spacer is the inner member of the stylet assembly that occupies the radial space between the lead's cable and the stylet and facilitates removal of the tools used in implantation of the lead. The stylet spacer is slidably accommodated in the lumen 43 of the stylet. Opening 39 of the stylet spacer accommodates cable 29. The stylet has a distal end 44, which cooperates with the proximally facing shoulder 33.

The reinforced portion of the cable is sized for a close fit in the distal portion of opening 39. The remaining portion of the cable is sized for easy sliding in opening 39 to allow withdrawal of the stylet spacer with a minimum of traction on the cable.

FIGS. 3A-D—Cable Construction

FIGS. 3A-D show examples of cross-sectional configuration of cable 29. With the stylet assembly being external to the cable, many cable constructions and conductor types are possible. In particular, stranded conductors (i.e., having multiple wire strands twisted together) can be easily employed. Cables constructed with stranded conductors have good flexibility and, in contrast to coiled conductors commonly used in implantable leads, provide better crush and kink resistance and allow a small minimum bend radius (important at the lead's exit from the burr hole and at the lead's entry into the proximal connector). The stranded conductors also have greater flexibility and higher tensile strength than single conductors having equivalent cross-section. While stranded conductors are shown, single-wire conductors or other known multi-strand conductor constructions can alternatively be used.

Figure 3:
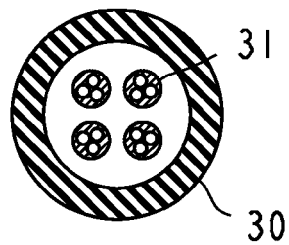
Figure 3:
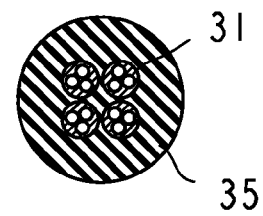
Figure 3:
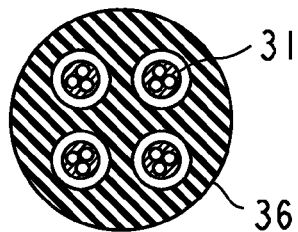
Figure 3:
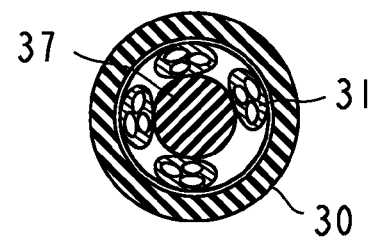

In FIG. 3A, conductors 31 are loosely fitted in the central lumen of insulating jacket 30. The conductors may be wavy or loosely wound along the lumen. The axial length of each conductor can thus be greater than the axial length of the cable body, so that no axial tension is applied to a conductor when the cable body is stretched to a length not exceeding the length of the conductor.

The wires can be made from a platinum-iridium alloy or other high tensile strength alloy suitable for use in chronically implanted stimulation leads. The diameter of individual wire strands may be 0.025 mm (AWG 50), 0.032 mm (AWG 48) or other desirable size. In an exemplary construction, utilizing 0.025 mm diameter wires, a three-wire stranded conductor may have a diameter of approximately 0.1 mm, including insulation. The overall diameter of a four-conductor cable can be 0.5 mm or less.

The individual wire strands may have a coating of insulating material, such as ethylene-tetrafluoroethylene (ETFE), another fluoropolymer, or polypara-chloroxylylene (sold under the trademark Parylene-C by Specialty Coating Systems, Indianapolis, Ind.), or other insulating material used for coating of implantable conductors. Multi-strand conductors may have additional collective coating or co-extrusion of insulating material to hold the multiple strands together. Alternatively, bare multi-strand conductors may have only a collective insulation which may be coated or co-extruded onto the conductors.

In FIG. 3B, conductors 31 are stranded together and embedded in an insulating jacket 35.

In FIG. 3C, each conductor is loosely fitted in a corresponding lumen in an insulating jacket 36.

FIG. 3D is another embodiment of a cable, having conductors 31 helically wound around a core 37 and placed in an insulating jacket 30. The core can be elastomeric to allow the cable to have stretchability in service. Such stretchability allows accommodation of movement (e.g., due to an articulated part of the body) and or tissue dislocation (e.g., due to atrophy or growth), and thus prevents build up of axial tension in the lead which could cause lead dislodgement. Alternatively, a core of a high tensile strength fiber such as aramid fiber can be used to reinforce the cable. Jacket 30 can be a discrete tube made from silicone rubber, polyurethane, or a similar elastomeric material.

FIGS. 4A-B—Reinforced Cable Portion

FIGS. 4A and 4B are cross-sectional views of a reinforced cable portion 34. The reinforcing provides a stiffened portion of the cable that can be coupled by the stylet assembly to constrain the electrode terminal from tilting and flexing. In addition, the reinforced portion of the cable provides a strain relief to the cable at the exit from the electrode terminal.

In FIG. 4A the distal portion of cable 29 is reinforced by an externally disposed tube 38 which extends from the electrode terminal body. The outside diameter of insulating jacket 30 entering the tube may be reduced to make a close fit or slight interference with the reinforcing tube. The jacket may also be attached to the reinforcing tube with an adhesive and/or the reinforcing tube may be crimped over the cable.

In FIG. 4B the jacket is placed over the reinforcing tube. The jacket may be stretched over the tube and/or may be adhesively attached or heat sealed onto the tube.

FIGS. 5A-B—Lead with External Stylet Assembly

FIG. 5A is a side view of lead 20 with the stylet assembly installed. Stylet 41 and stylet spacer 42 are slipped over cable 29 so that the distal end 44 of the stylet and the distal end of the stylet spacer are in contact with the shoulder 33 of the stepped portion 32.

The stylet and stylet spacer have permanently attached handles 45 and 46, respectively. The stylet is captivated between shoulder 33 and the stylet spacer's handle so that the distal end of the stylet remains in contact with the shoulder when the lead is advanced or retracted by pushing or pulling on the stylet spacer's handle.

The stylet assembly is coupled to the lead to allow retraction of the lead by pulling on the stylet assembly. The coupling means can be a friction or interference fit between the stylet spacer and the reinforced section of the lead, a shearable adhesive, or a screw clamp as disclosed below.

The external stylet is designed for a direct sliding contact with the cannula used to guide the lead into the target tissue. The outside diameter of the tubular stylet is thus maximized (for a given cannula lumen) and provides a stiffness that is at least two orders of magnitude (100 times) greater than the stiffness of a wire stylet in a conventional iso-diametric lead having comparable overall lead diameter. The substantial external stylet provides the requisite stiffness for introduction of the lead without the cannula entering the target tissue.

In order to assure desired pointing accuracy (i.e., the ability of the distal tip of the lead to follow the insertion trajectory defined by a cannula or a guide bushing) the electrode terminal must be prevented from excessive tilting and flexing relative to the central axis of the stylet. This is achieved by coupling the reinforced portion of the cable to the stylet, preferably with a minimal radial clearance. A slight interference fit or a shearable adhesive can be used to retentively engage the stylet spacer with the reinforced cable portion 34 while eliminating the radial clearance between these components.

FIG. 5B is an enlarged view of FIG. 5A with the stylet and stylet spacer shown in longitudinal cross-section. The reinforced portion of the cable body couples to the distal portion of stylet 41 via stylet spacer 42. The electrode terminal is thus constrained to remain substantially coaxial with the stylet. The cross-sectional views of the reinforced portion of the cable and stylet assembly are shown in FIGS. 7-8.

The stylet, the stylet spacer, and the corresponding handles can be made from a surgical stainless steel. The handles can be attached to the respective stylet and stylet spacer by a laser welding, crimping, or other known method. Alternatively, the handles can be made from a polymer and can be molded-on or adhesively attached to the respective stylet and stylet spacer.

FIGS. 6-10—Stylet Assembly Retentive Engagement with Lead

FIGS. 6A-B are partial cross-sectional views of a lead-stylet assembly having a built-in spring coupling mechanism.

The distal portion of a stylet spacer 47 is bifurcated into two end portions 48a and 48b having arcuate cross-sections as shown in FIGS. 9-10. The end portions are formed as shown in FIG. 6A to provide a spring coupling between the stylet assembly and the reinforced portion of the lead. When the stylet is slipped over the reinforced portion of the cable with the spacer present (as indicated by arrows in FIG. 6A), the formed spacer ends are resiliently compressed to retentively couple the stylet assembly to the reinforced portion of the cable. Alternatively, the distal portion of the spacer can be split into more than two end portions or have other formed features that provide controlled amount of interference or friction between the stylet assembly and the reinforced portion of the cable.

FIGS. 7-8 are cross-sectional views of the lead-stylet assembly utilizing tubular stylet 41 and stylet spacer 42. The cross-sections are taken across the reinforced portion of the cable. The stylet spacer is radially interposed between the reinforced portion of the cable and the stylet and couples the reinforcing tube to the stylet. The coupling constrains the electrode terminal to be coaxial with the stylet and thus helps to maintain the electrode terminal on the insertion trajectory defined by the lead introduction tools.

In FIG. 7, the most distal portion of the stylet spacer and the reinforced portion of the cable are retentively engaged by a thin layer of a shearable adhesive 49. The retentive engagement can be made adjacent to shoulder 33. The adhesive also removes the radial clearance between the spacer and the reinforced portion of the cable body, and thus minimizes tilting of the electrode terminal relative to the spacer. The remaining length of the reinforced portion of the lead is slidably coupled to the spacer as indicated by a small radial clearance between these components in the cross-sectional view of FIG. 8.

The adhesive can be silicone elastomer, epoxy, or the like. The adhesive is sheared when the stylet spacer is pulled while the stylet is immobilized. The shearing force can be on the order of several Newtons. Such spacer withdrawal force is tolerable since the stylet holds the electrode terminal from retracting when the spacer is forcibly removed after the lead is successfully localized.

Alternatively, the reinforced portion of the cable may be retentively engaged in the lumen of the stylet spacer by a slight interference or friction fit. Still another method of preventing unintended separation of the stylet assembly from the lead, wherein the proximal end of the cable is coupled to the proximal end of the stylet, is disclosed in the section titled Lead Introduction Tools for Leads with External Stylet.

FIGS. 9-10 show cross-sectional view of the lead-stylet-sleeve assembly utilizing a bifurcated distal end of the stylet spacer comprising formed end portions 48a and 48b. The compressed arcuate end portions are in a simultaneous retentive contact with the stylet (FIG. 9) and the reinforced section of the cable (FIG. 10).

FIGS. 11-12—Electrode Terminal Construction

FIGS. 11-12 show an embodiment of a small-dimensioned electrode terminal 23 comprising closely spaced electrodes 25, insulating body 24, and a distal tip 51. As a non-limiting example, the electrode terminal's diameter may be 1.0 mm, the electrode's length may be 1.0 mm, and the electrode pitch may be 2.0 mm. Such small-dimensioned electrode terminal is desirable for implantation in a small and/or dense anatomical target where a high spatial resolution is required for electrode localization.

The electrode material can be platinum, platinum/iridium, or the like. Tube 38 is preferably made out of metal but can also be made from a high modulus or reinforced polymer. If the reinforcing tube is made from a conducting material, the tip may form at least a portion of the most distal electrode or may provide a separate tip electrode. Such tip electrode can be connected to a corresponding contact of the connector terminal and used as one of the device's electrodes. Alternatively, the tip electrode may be dedicated for use with a recording microelectrode and/or for test stimulation.

The cross-sectional view of FIG. 12 shows internal construction of electrode terminal 23 which is also applicable to any electrode terminal with a centrally exiting cable. The reinforcing tube 38 stiffens the electrode terminal and provides the structural support for the terminal assembly. The tube accommodates the conductors of cable 29 and, depending on the cable's outside diameter, may also accommodate a portion of the cable's jacket 30, as shown. The inside of the tube can be potted with potting compound 52 to form a relatively solid core or can be filled with the insulating body material when insulating body 24 is formed. The optional potting is indicated by a dotted hatch in order not to obscure the internal construction of the electrode terminal.

The reinforcing tube has a lengthwise slot 53 (better seen in FIG. 13) along the length adjoining the electrodes to provide a passage for the conductors to allow them to be connected to respective electrodes 25. The distal tip 51 can be attached to the reinforcing tube by a joint 54 or formed as a portion of insulating body 24.

In addition to providing a small dimensioned and stable core for the electrode terminal construction, the reinforcing tube also stiffens the distal portion of the cable and provides a means for coupling the electrode terminal to the stylet assembly. The proximal end of the reinforcing tube extends proximally from the electrode terminal so that the electrode terminal and the distal portion of the cable have common stiffening means. Once the reinforced portion of the cable is coupled to the stylet assembly (FIGS. 7-10), the external stylet constrains the most distal portion of the lead from flexing and tilting. The coupling minimizes the deviation of the electrode terminal from the intended trajectory set by the lead introduction tools when the lead is being introduced. The length of the coupling should be adequate to assure a desired pointing accuracy for the distal end of the lead as it advances through the tissue.

Exclusion of the stylet from the electrode terminal reduces the outside diameter of the electrode terminal and consequently allows to reduce the diameter of the electrodes. The lead can thus have a small-dimensioned electrode terminal without sacrificing the lead's pointing accuracy. The requisite stiffness is provided by the reinforcing tube coupled to the external stylet assembly.

An insulating interliner sleeve 55 is installed over the reinforcing tube. The interliner can be a sleeve of an insulating material having a lengthwise slit, so that after it is placed on the reinforcing tube, a lengthwise opening 56 (FIG. 13) is created to provide a passage for the inserts. If the reinforcing tube is conductive, the slit in the sleeve can be made somewhat narrower than the slot in the tube, so that the inserts can be held in-line without contacting the reinforcing tube.

The interliner provides a thin layer of insulation which maintains the electrodes and the reinforcing tube in a coaxial relationship and helps to neatly arrange the conductors which are contained within the lengthwise opening. The interliner can be made from a thin polyimide tubing, with wall thickness of approximately 0.1 mm, or less. The interliner provides a thin and effective layer of insulation which would be impractical to obtain by other techniques, e.g., overmolding. Use of the interliner results in a compact electrode terminal construction and minimizes fixturing required for the assembly. Electrodes 25 are placed over the interliner tube with a close fit so that the electrodes are radially constrained relative to the core. This arrangement is space efficient and assures concentricity of the reinforcing tube and the electrodes.

Each conductor can be terminated to the respective electrode using an insert. Conductor 31 is joined to an insert 57 which in turn is joined to electrode 25. Insert 57 is button-shaped and is accommodated in a cross-hole 58 (better seen in FIGS. 13-15) in the electrode, where it is joined to the electrode, preferably by laser welding as indicated by a weld 59. Additional insert embodiments and associated termination techniques are disclosed in separate sections below.

FIGS. 13-15—Conductor Attachment to Electrode

FIGS. 13-15 detail the insert construction and attachment to the electrode. Insert 57 is substantially round and has a wire termination side 60 and a weld side 61. The wire termination side may have a slot or channel 62 to facilitate receiving and joining a bared end 63 of conductor 31. A stranded three-wire conductor is shown but a single wire or any other known biocompatible conductor construction can be used. At least the weld side of the insert is substantially round and sized for a close fit in cross-hole 58. The termination side is shown round and having a larger diameter than the welding side so that a shoulder 64 is created. The shoulder prevents penetration of the laser energy to the termination side of the insert and can be used to stop the insert against the inner surface of the electrode. However, the termination side does not need to be round or have a termination slot. In its simplest form the insert could be a cylindrical button with flat top and bottom sides.

In order to attach a conductor-insert pair to an electrode, the insert is brought into the opening of the electrode and is inserted into cross-hole 58. A chamfer 65 facilitates insertion of the insert into the cross-hole, and shoulder 64 provides a positive stop. The weld side of the insert may be slightly recessed below the outside surface of the electrode, as shown in FIG. 13, to assure that weld joint 59 does not protrude beyond the outer surface of the electrode.

Returning to the construction of electrode terminal 23, the conductor-insert harness can be prepared separately, i.e., apart from electrodes and other components. A desired length of conductors 31 is stripped of the cable's jacket and each conductor is cut to length according to the electrode spacing in the lead. The conductor ends are bared (stripped of insulation) and terminated to the inserts. The inserts are thus disposed in a linear pattern and are spaced consistent with the electrode pitch in the electrode terminal.

FIGS. 16A-C—Electrode Terminal Assembly

FIGS. 16A-C show the electrode terminal at three stages of construction. In FIG. 16A the conductor-insert harness is shown inserted into the reinforcing tube 38.

In FIG. 16B, interliner sleeve 55 and the electrodes are added. The lengthwise slit in the interliner is aligned with the slot in the reinforcing tube to maintain a passage for the conductor-insert pairs. The electrodes are slipped over the interliner sleeve and aligned with the inserts. The inserts, with wires attached, are taken out of the tube through slot 53 and are inserted into the cross-holes of the respective electrodes where they are attached to the electrodes, preferably by laser welding. If the diameter of the cable is smaller than the inside diameter of the tube, the electrodes can be pre-attached to the conductor-insert harness and thus obtained conductor-insert-electrode harness can be inserted into the reinforcing tube from the slotted end of the tube.

The material of the electrode terminal body can be silicone rubber, polyurethane, a silicone-urethane copolymer, or the like. Other biocompatible polymers, such as polyetheretherketone (PEEK) can also be used since, in contrast to the cable's insulating body, the relatively short high definition electrode terminal does not need to be flexible. The insulation can be added by overmolding or, if a thermoplastic such as polyurethane is used, can be added in a discrete form and heat-formed or heat-sealed in place.

After all electrodes are in place, distal tip 51 is added and attached to the reinforcing tube by an applicable method such as laser welding, ultrasonic welding, or adhesive. Finally, the electrodes are set to the desired positions by fixturing or other method (such as adhesive tacking) and the assembly is overmolded to form insulating body 24.

FIGS. 17A-B—Lead with a Sheath

In the embodiment disclosed below the lead further comprises a sheath which accommodates the distal portion of the stylet spacer. The sheath can be made from the same or similar material as the electrode body's overmolding and may be added by overmolding or may be molded separately and fused to the body of the electrode terminal by heat sealing or bonding.

FIG. 17A is a perspective view of a lead embodiment 70 comprising a tubular sheath 71 having an opening 72 and outer end 73 which serves as a shoulder for the stylet. Multi-conductor cable 29 extends inside the sheath opening toward electrode terminal 23.

FIG. 17B is a partial cross-sectional view of lead 70 with stylet assembly installed. Stylet spacer 42 accommodates the centrally disposed cable 29. The distal portion of the stylet spacer slidably engages reinforced portion 34 of the cable. The distal end 44 of the stylet is in contact with outer end or shoulder 73 of the sheath. The stylet spacer is slidably received in the central lumen of the stylet.

The distal end of the stylet may bear on the outer end of the sheath when the lead is being advanced into the tissue. When the stylet spacer must be removed, the stylet is immobilized to constrain the lead from retracting. By holding the outer end of the sheath in place with the stylet and pulling on the stylet spacer, the stylet spacer can be released from the sheath. This functionality facilitates lead introduction and minimizes dislodgment of the implanted lead due to removal of the stylet spacer.

FIGS. 18-20—Lead with a Sheath-Cross-Sections

FIGS. 18-20 are cross-sectional views of lead 70, with the stylet assembly installed, at various locations along the lead as indicated in FIG. 17B.

The cross-section of FIG. 18, taken at the reinforced portion of the cable and the sheath, shows reinforcing tube 38, stylet spacer 42, and sheath 71 in a slidable (easily disengageable) contact, as indicated by small radial clearances between these components.

The cross-section of FIG. 19, taken near the outer end of the sheath, shows the stylet in retentive contact with the sheath as indicated by a surface-to-surface contact between these components. The retentive contact can be obtained by making the inside diameter of the sheath at the outer end slightly smaller than the outside diameter of the stylet. Alternately, or in addition to a slight interference, a shearable adhesive interface can be used to provide the desired stylet spacer retention at the outer end portion of the sheath. Outside the retention area, the diameter of the sheath opening is slightly larger than the diameter of the spacer body, allowing removal of the spacer with minimal traction on the sheath after the retention mechanism is released.

The retentive fit between the spacer and the sheath provides a self-contained retention mechanism (no additional parts, such as a stylet retainer used in prior art) and minimizes internal lead displacements due to traction and axial compressibility and/or stretchability of the lead. Since the stylet must provide both advancement and retraction of the lead, the retentive force must exceed the maximum traction on the retracting lead in order to prevent an unintended release of the stylet from the lead.

The cross-section of FIG. 20, taken outside the sheath, shows stylet 41 slidably accommodating stylet spacer 42. The outside diameter of the stylet matches the outside diameter of the sheath, so that both the stylet and the sheath can be guided in a lumen of a cannula 125 (FIG. 32A).

FIGS. 21-25—Termination of Conductors to Electrodes using Tubular Inserts

An important aspect of miniature lead construction and fabrication is the termination (connection) of conductors to electrodes and contacts. A direct termination of coiled conductors to ring electrodes is well known in the art. In a typical process, each coiled conductor is unwound from the coil, bared at the end, and routed to a respective electrode where it is welded in a small groove adjacent to the outer surface of the electrode. However, the presently practiced termination techniques are difficult when lead diameter is less than 1.0 mm and electrode spacing is less than 2.0 mm. In addition, a very small joint adjacent to the electrode's outer edge is fragile and susceptible to damage due to flexing or buckling of the lead. While further miniaturization of leads is desired, a direct termination of very fine single-wire conductors or stranded conductors is problematic and in need of solution. Using the disclosed inserts provides a robust method of terminating the conductors to electrodes and facilitates fabrication of the lead.

The inserts are particularly advantageous for termination of stranded conductors, allowing the conductors to be joined easily and reliably to a relatively large area of the insert. The insert and the electrode can be nested together to facilitate their alignment and joining and to promote an efficient use of available space.

The inserts can be made from the same or similar material as the electrodes, e.g., platinum or platinum-iridium, and can be economically produced by coining, stamping, or machining FIGS. 21-23 show an insert 80 which has a tubular body 81 with a necked portion 82 adapted for accommodating and crimping bared end 63 of conductor 31. The hole 83 is sized to receive insulated portion of the conductor in the body portion which may optionally be crimped to provide strain relief for the connection. In order to join the conductor-insert pair to an electrode 84, the body of the insert is nested in an arcuate cut 85 on the inside surface of the electrode and welded to the electrode at a cross-hole 86. The resulting weld 87 is shown in FIG. 22.

FIGS. 24 and 25 show insert variations 88 and 89 respectively, that can be attached to electrode 84 in the manner similar to that described for insert 80, i.e., by nesting the insert in arcuate cutout 85 and welding at cross hole 86. Insert 88 has arcuate profile throughout while insert 89 is partly arcuate and partly tubular. A bared conductor can be attached to these inserts by welding, soldering, conductive adhesive, or other known method.

Figure 26:
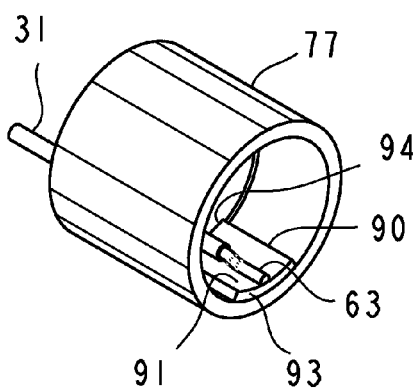
Figure 26:
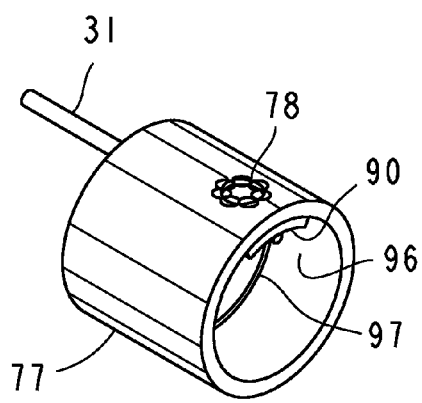
Figure 27:
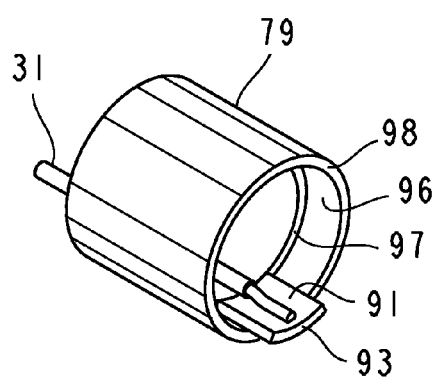
Figure 27:
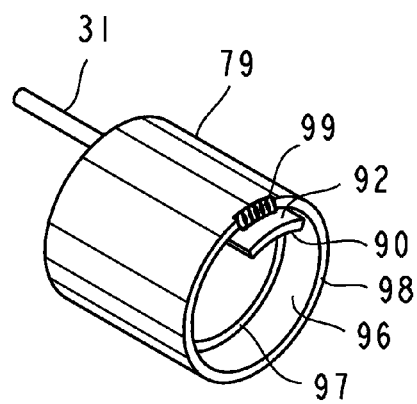

FIGS. 26-27—Termination of Conductors to Electrodes using Arcuate Inserts

FIGS. 26A-B and 27A-B demonstrate use of arcuate inserts. Insert 90 has a generally arcuate form with an inner surface 91, an outer surface 92 (FIG. 27B), a front edge 93 and a back edge 94. The end of conductor 31 is stripped of the insulation to provide a bare end 63 which is joined to the insert at inner surface 91. The conductor ends can be bared by mechanical stripping, laser ablation, or any known method that cleanly and neatly removes insulation from fine wires. The large conductor attachment area provided by the insert enables a robust joint and makes it possible to use a variety of termination techniques. Stranded or solid conductors can be terminated by any known method used for stranded or solid conductors including laser or resistance welding, soldering, thermosonic bonding, crimping, and conductive adhesive bonding. After joining, the conductor-to-insert joint may be strain-relieved by encapsulating or coating the joint with an adhesive.

The conductor-insert assembly can be fabricated apart from the electrodes and other lead components. The required number of conductor-insert pairs can be assembled in a predetermined arrangement consistent with the electrode spacing in the electrode terminal. The conductor-to-insert terminations can be easily inspected and tested. The thus prepared conductor-insert harness is nested with the electrodes, and the outer surface of each insert is joined to a respective electrode 77.

FIGS. 26 A-B show a terminated insert-conductor pair joined to electrode 77. The electrode is counterbored to form a recessed surface 96 and a step 97. The outer surface of the insert and the recessed surface of the electrode have complementary curvatures and can be nested together. Step 97 can be used to locate the back edge of the insert. FIG. 26B shows the insert joined to the electrode at cross-hole 78, e.g., by laser welding.

Alternatively, the insert may be joined to the electrode as shown in FIGS. 27A-B. The insert is placed in recess 96 so that front edge 93 of the insert protrudes beyond rim 98 of the electrode 79. The distance by which the insert protrudes from the electrode can be set by step 97. The outer surface 92 of the insert is then attached to the rim of the electrode by weld line 99.

FIGS. 28-29—Termination of Conductors to Electrodes using Co-Planar Inserts

FIGS. 28A-C show another embodiment of an insert and a method of assembly. An insert 101 is in a form of a blank, designed to be accommodated in a complementary cutout 102 in an electrode 103. The insert has an inner surface 104, an outer surface 105 and a back edge 106. The remaining edges 107 of the insert are profiled to match the cutout in the electrode. The conductor is attached to the inner surface 104 using one of the methods listed for the arcuate inserts discussed above, e.g., laser welding.

The insert is joined to the electrode at cutout 102, e.g., by laser welding. The resulting weld line 108 is shown in FIG. 28C. After attachment to the electrode, the outer surface of the insert is substantially co-planar with the outer surface of the electrode. The back edge 106 of the insert is preferably aligned with the outer edge 109 of the electrode. If insert 101 is small, it does not need to have the same outer curvature as the electrode since the insert edges will be largely consumed by the weld line. It is desirable, however, that the insert and the weld line are smooth and within the electrode's outside diameter.

FIG. 29 shows an insert 110 having a slotted portion 111 for captivating conductor 31. The slot holds the conductor for termination and provides a strain relief for the joint.

FIG. 30 shows bare end 63 of conductor 31 attached directly to the inner surface 112 of an electrode 113.

FIGS. 31A-C—Connector Terminal Assembly

The connector terminal allows the lead to electrically connect to an implantable device and, if desired, can also be accessed intra-operatively by an external instrumentation such as a screening unit or a test stimulator. The construction of the connector terminal can be substantially the same as the construction of the electrode terminal disclosed above. In general, the disclosed methods of reinforcing the electrode and connector terminals and the use of inserts to terminate conductors can be used interchangeably in the connector and electrode terminals.

FIGS. 31A-C show an embodiment of connector terminal 26 at three stages of assembly. In FIG. 31A the conductor-insert harness is shown inserted into the reinforcing core 115. The conductor-insert harness can be fabricated prior to the insertion into the core. The reinforcing core has a lengthwise channel 116 into which the conductors are accommodated. The top of the channel has rails 117 adapted to locate and hold inserts 90. The distal portion 118 of the channel can be adapted to accommodate a small portion of cable 29.

In FIG. 31B, electrodes 77 are added. The electrodes are slipped over the reinforcing core and aligned with the inserts. Each electrode is joined to the respective insert by weld joint 78 at the electrode's cross-hole.

In FIG. 31C connector terminal body 27 is formed by overmolding the assembly of FIG. 31B. The proximal tip 119 can be an integral part of the core or can be formed by the overmolding.

The material of the connector terminal body can be silicone rubber, polyurethane, a silicone-urethane copolymer, polycarbonate urethane (Bionate), polyetheretherketone (PEEK), or the like. The reinforcing core can be made from polyetheretherketone (PEEK), high durometer polycarbonate urethane (Bionate 75D), or the like FIGS. 32A-B—Lead Localization using Stereotactic Guidance As described in the prior art section, a stereotactic frame is typically used to identify the location of the lead entry into the brain and to facilitate the implantation of the lead. The system enables the lead to be localized using a technique called stereotaxy, a method of locating points within the brain using a stereotactic frame as an external three-dimensional frame of reference based on the Cartesian coordinate system.

FIGS. 32A and 32B show a system for introduction and accurate positioning of a lead into the brain 120, utilizing a cannula 125 that is held outside of the brain. The relatively substantial external stylet is sufficiently stiff to provide a desired pointing accuracy without using a brain-entering cannula. The cannula has a distal end 126 and a central lumen 127 for slidably guiding the lead-stylet assembly into the target tissue.

The stereotactic system employs a stereotactic arc 131 which is attached to a stereotactic frame (not shown) which is rigidly mounted on the patient's head. The stereotactic arc instrumentation, shown simplified, is a part of a stereotactic system sold by Elekta corporation, Stockholm, Sweden, under the trademark Leksell. The stereotactic arc has a guide holder 132 and a stop holder 133 which are slidably mounted in an instrument carrier 134.

After a burr hole 135 in the cranium 136 and an entry opening in the dura mater are created, a lead anchoring ring (not shown) may be placed in the burr hole. The stereotactic arc is then instrumented with a cannula guide 137 holding cannula 125, and a stop bushing 138.

The cannula is lowered so that the distal end of the cannula is just outside the cranium. Since the cannula is completely external to the brain, it is advantageous to bring the distal end of the cannula as close to the cranium as possible, even in contact with the cranium. If desirable, the outside diameter of the cannula may be larger than the burr hole, or larger than the opening in the pre-installed anchoring ring, to preclude the cannula from entering the brain.

A lead-stylet assembly, e.g., comprising lead 20 and stylet assembly 40, is passed through the center bore of stop bushing 138 and through the lumen in cannula 125. From the initial position shown in FIG. 32A, the lead is advanced along the insertion trajectory until stylet handle 45 arrives at stop bushing 138. The stop bushing position is set so that when handle 45 is at the stop bushing, the distal tip of the lead is at the desired initial location along the insertion trajectory, e.g., just above a predetermined location of the anatomical target in the brain. The desired stop bushing position can be set knowing that, when the arc is attached to the frame, the target location corresponds to the center of the stereotactic arc.

Once at the desired initial location (FIG. 32B), the lead is advanced in small incremental steps and an intra-operative test stimulation is performed to verify the desired response. The lead's current insertion depth may be indicated by a scale 140 on the sliding arm of the stop holder, indexed to a fixed reference mark on the instrument carrier. If desired, the stylet may also have graduated marks 141 to allow monitoring of the lead's advancement into the brain by reference to the top surface of the stop bushing or other stationary reference.

FIGS. 33A-B—Lead Introduction Tools for Lead with External Stylet

FIGS. 33A-B correspond to FIGS. 32A-B respectively, but are enlarged partial views to show the lead introduction tools in further detail. Spacer handle 46 is coupled to the lead with a screw 145 or other coupling means, such as a spring loaded plunger. A leaf spring 146 can be interposed between the screw and the cable to avoid direct contact between the screw and the cable and to assure that the cable is positively released when the screw is unclamped. The stylet is captivated between the distal side of spacer handle 46 and the shoulder of the stepped portion 32 of the lead. Alternatively, the stylet can be disengageably attached to the spacer by a set screw or other attaching means (not shown). The reinforced portion of the cable may also be retentively engaged with the distal portion of the stylet spacer, e.g., by a slight interference fit or shearable adhesive 49 (FIG. 7).

Stylet handle 45 has a neck 147 sized to be slidably received in the counterbore 148 of the stop bushing. The neck may have a notch 149 to facilitate locking of the stylet handle in the stop bushing. The notch can be circumferential or localized (e.g., a countersink or a counterbore at a specific location on the circumference) if it is desirable to prevent the stylet from rotation in the stop bushing.

When stylet handle 45 arrives at stop bushing 138, the stylet handle can be locked to the stop bushing with a screw 150 or other locking means (FIG. 33B). The screw may have a spring loaded plunger 151. The tip of the screw (or plunger 151) cooperates with notch 149 to securely lock the stylet handle in the stop bushing. The lead can now be incrementally advanced toward the target using a fine motion of the stop holder or using a microdrive (not shown) attached to the stop holder. The final lead localization in the target is performed using known techniques and is verified by test stimulation.

After successful localization of the lead is confirmed to be efficacious, the remaining steps of the procedure must not alter the lead's position in the stimulation target. In particular, the disassembly and removal of the lead introduction tools and the anchoring of the lead at the exit from the burr hole must not dislocate the lead.

At the conclusion of the lead localization, the stop holder 133 is locked in the instrument carrier of the stereotactic arc (FIG. 32B) thus immobilizing stop bushing 138. The stylet spacer can now be disengaged from the lead by releasing the coupling between the spacer handle and the cable (e.g., unclamping screw 145) and pulling on spacer handle 46 to retract the spacer while the stylet is immobilized in the stop bushing. The pulling action releases the retentive grip between the spacer and the reinforced portion of the cable if such retentive grip is employed. Since the lead is immobilized by the stylet when the spacer is being removed, the spacer can be released and/or removed without causing dislodgement of the lead.

The removal of the stylet creates a radial clearance between the cable and the stylet. The radial clearance allows subsequent removal of the stylet and the cannula without generating a drag or fraction on the lead. The stylet can be removed by unlocking and raising the stop holder or by unlocking the stylet handle from the stop bushing (e.g., unclamping screw 150) and pulling on the stylet handle.

FIGS. 34A-B—Lead Introduction Tools for Lead with Segmented Spacer

FIG. 34A-B are partial cross-sectional views of the lead introduction tools adapted for introducing a lead with stylet spacer comprising two spacer segments. The stylet spacer has two, preferably identical, spacer segments 142a and 142b. Each spacer segment has an arcuate cross-sectional profile having included angle of less than 180°, as shown in FIG. 36. The proximal ends of the spacer segments may be bent and may have molded-on or attached handles 143a and 143b on respective ends. Stylet handle 152 is adapted to couple to the lead by clamping the spacer segments against the lead using screw 145 (FIG. 36).

The lead can be introduced using the procedure described in connection with FIGS. 33A-B. Similarly, the spacer segments can be disengaged from the lead by releasing the coupling between the spacer handles and the cable (e.g., unclamping screw 145) and pulling on the spacer handles 143a and 143b to retract the stylet segments while the stylet is immobilized in the stop bushing. Since the lead is immobilized by the stylet when the spacer segments are being removed, the spacer segments can be released and removed without causing dislodgement of the lead.

Figure 35:
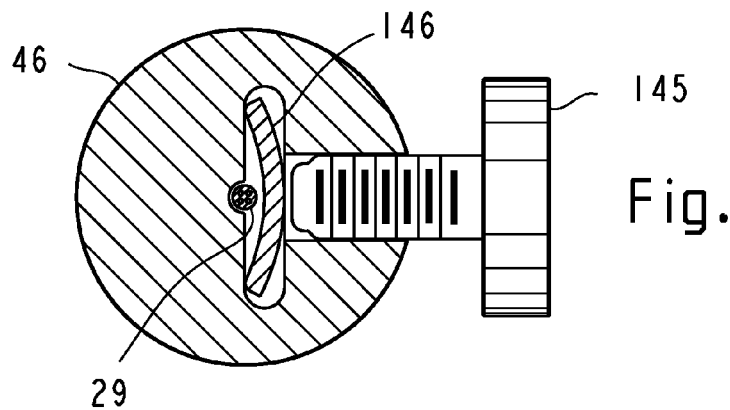
Figure 35:
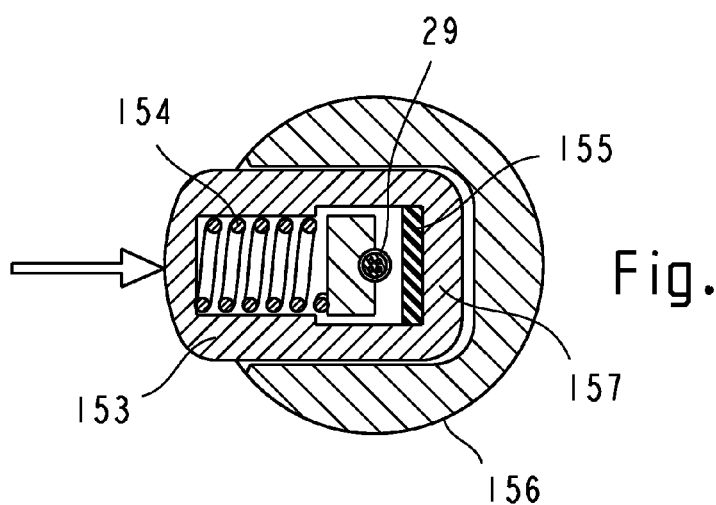

FIGS. 35-36—Coupling of Stylet Assembly to Lead—Cross-Sections

FIG. 35A shows a cross-sectional view of the coupling mechanism between the stylet assembly and the lead in FIG. 33A. When leaf spring 146 is clamped by screw 145, cable 29 is locked in spacer handle 46 and will advance and/or retract with the stylet assembly. In a clamped condition, the leaf spring is substantially flat and closes the pocket confining the cable. The depth of the pocket is selected so that the cable cannot be over-clamped. The leaf spring protects the cable from a direct contact with the screw. When the leaf spring is unclamped (as shown), it returns to the arcuate shape, positively releasing the cable from the stylet assembly.

FIG. 35B shows an alternate coupling mechanism between the stylet assembly and the lead of FIG. 33A. The quick release coupling mechanism comprises a body 153, a spring 154, and a resilient lining 155. Cable 29 is disengaged from a handle 156 when the spring loaded body is depressed in the direction indicated by the arrow. When the pressure is released, the spring pressure forces the back portion 157 of the body to lock the lead in the handle. The elastomeric lining protects the lead from damage and enhances the coupling by increasing the friction at elastomer-to-lead interface.

FIG. 36 shows a cross-sectional view of the coupling between the stylet assembly and the lead in FIG. 34A. When the cable is clamped between spacer segments 142a and 142b with screw 145, the cable and the spacer segments are locked in handle 152 and will advance and/or retract with the stylet assembly. The bottom 158 of the screw hole stops the tip of the screw and thus prevents over-clamping of the cable. The spacer segments protect the cable from direct contact with the screw. When the screw is unclamped the spacer segments are decoupled from the stylet assembly and can be removed.

Figure 37:
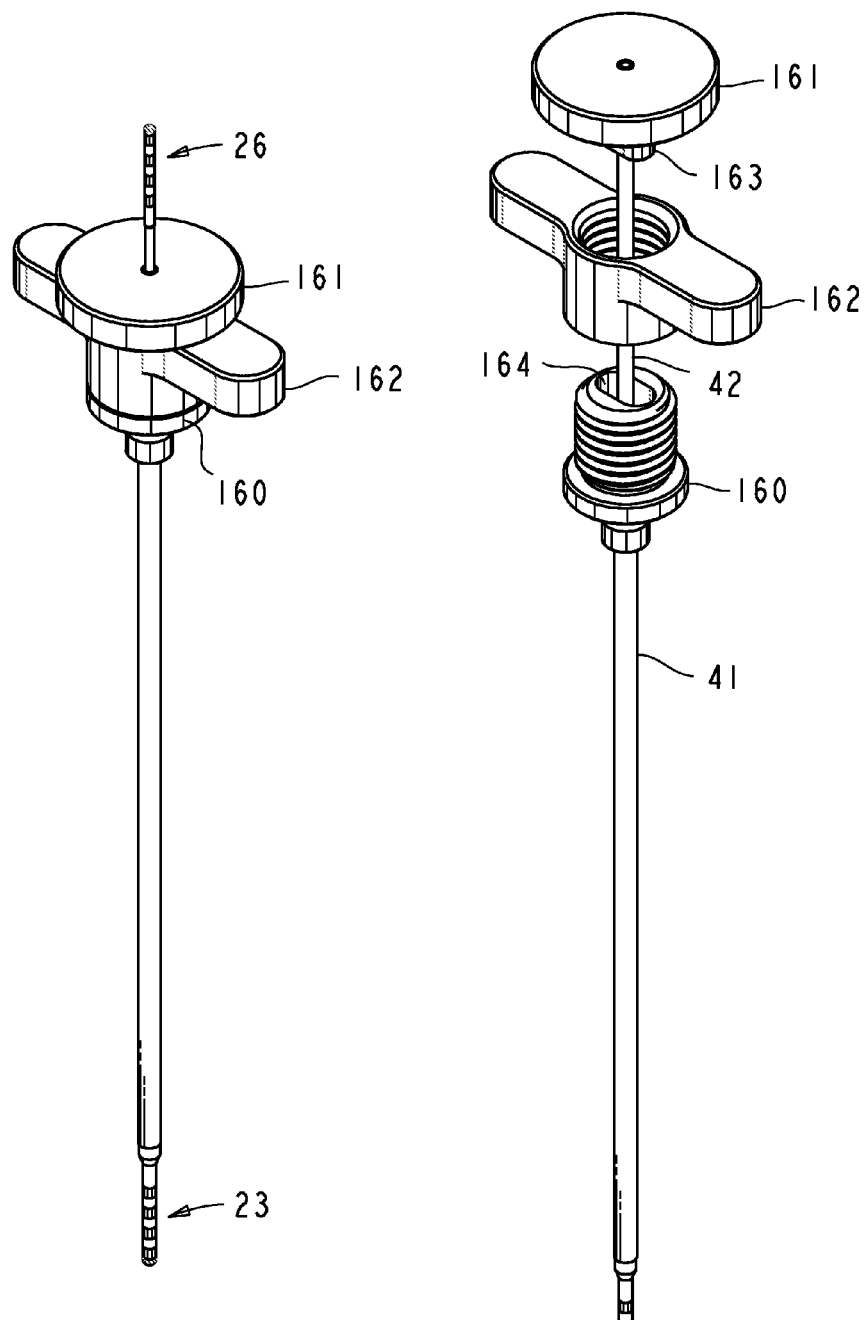

FIGS. 37-38—Stylet Assembly with Stylet Disengagement Mechanism

Some disclosed leads may be retentively engaged with their stylet assembly. In such cases a spacer disengagement mechanism can be used to facilitate the release of the spacer from the lead after the lead is implanted.

FIG. 37A shows a lead-stylet assembly having a spacer disengagement mechanism utilizing the mechanical advantage of a threaded connection. FIG. 37B shows the cooperating components of the disengagement mechanism in an exploded view. The disengagement mechanism comprises a threaded stylet handle 160, a spacer handle 161, and a driving nut 162. The spacer handle further has a guide key 163 cooperating with a guide hole 164 of the stylet handle. The spacer handle and the stylet handle are permanently attached to the spacer and the stylet respectively, as discussed above.

FIGS. 38A-B are partial cross-sectional views showing the lead-stylet assembly of FIG. 37A (having a spacer disengagement mechanism) interfaced with the lead introduction tools. The lead introduction tools and the lead introduction steps are substantially the same as those discussed in connection with FIGS. 33A-B. At the conclusion of the lead localization, the introduction tools are configured as shown in FIG. 38B. Stylet handle 160 is locked in stop bushing 138 using screw 150. Guide key 163 is engaged in guide hole 164 so that the stylet handle is prevented from rotation. The proximally facing surface of the driving nut is in contact with the spacer handle.

The retentive engagement between the spacer and the lead can be released by rotating the driving nut counterclockwise which pushes on the spacer handle and thus forces the spacer to retract. A gradual retraction of the spacer enables the retentive grip to be overcome in a controlled manner. Once the retentive grip is released, the stylet spacer can be easily removed by pulling on the spacer handle 161 while the stylet is still immobilized and holds the lead from retracting. After the spacer is removed, the stylet can be retracted by releasing the locking screw 150 and pulling on stylet handle 160. The driving nut provides a convenient handle for pulling on the stylet.

Figure 40:
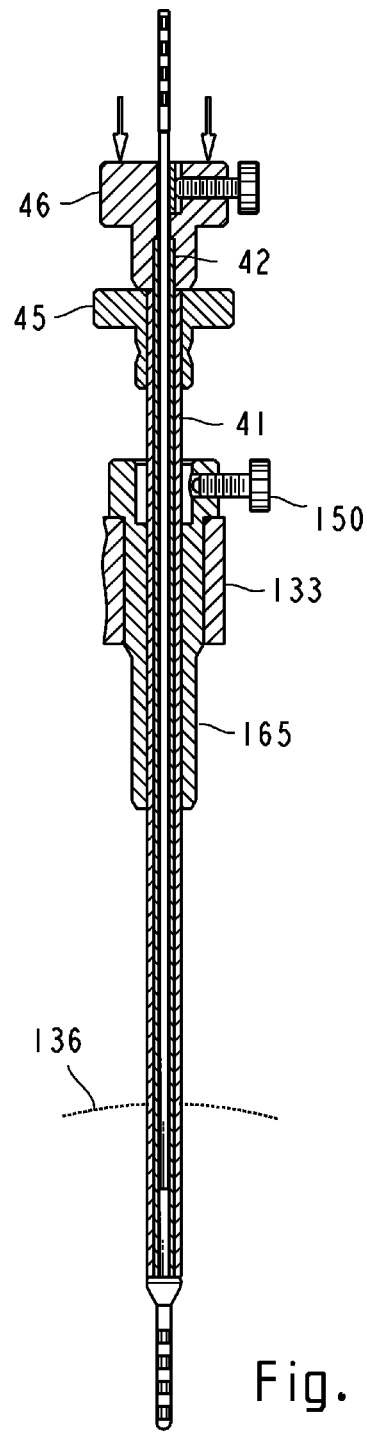
Figure 40:
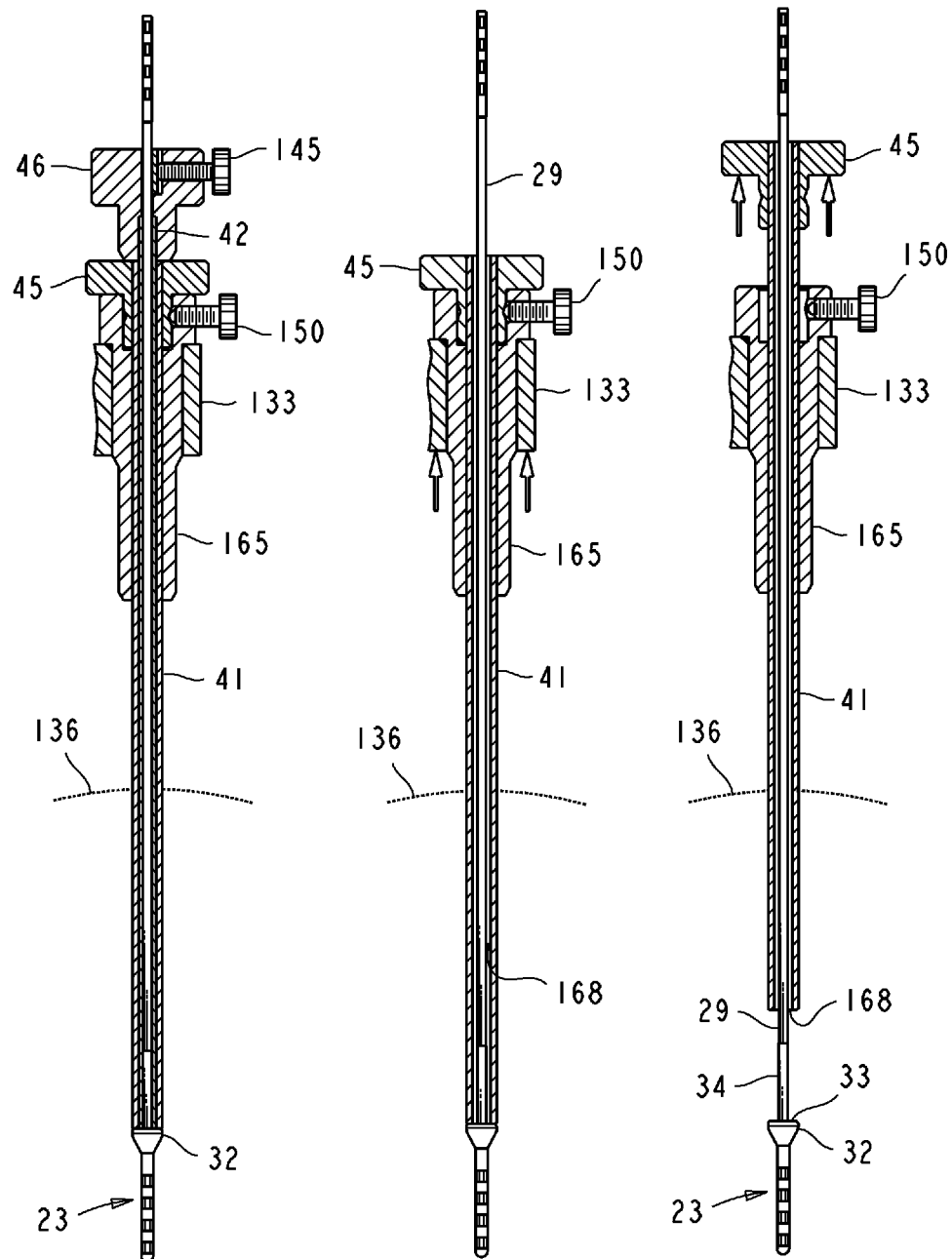

FIGS. 39-40—Lead Introduction without Using Cannula

The external stylet can provide sufficient stiffness to allow introduction of the disclosed leads without the use of a cannula. In contrast to the internally disposed stylet of prior art (FIGS. 1A-B) which is limited by the size of the lead's central lumen, the outside diameter of an external stylet can be made larger without increasing the cross-sectional dimensions of the lead.

The elimination of the cannula simplifies lead introduction tools and the lead introduction procedure. The minimum required cable length is significantly reduced. A cannula-free lead introduction can also be advantageous for introduction of leads into anatomical targets other than the brain or when a stereotactic instrumentation is not used.

FIG. 39 is a lead introduction system equivalent to that in FIG. 33A, with the cannula eliminated and the cannula guide bushing adapted to slidably guide the stylet. Stylet 41 may have a slightly larger outside diameter than its counterpart in FIG. 33A to compensate for the elimination of the cannula.

FIG. 40A shows an embodiment of a lead introduction system which is a variation of that in FIG. 39 with the guide bushing eliminated. A single stop bushing 165 combines the functionality of stop bushing 138 and guide bushing 137. The length of stop bushing 165 is increased to provide more guidance for the stylet. Elimination of both the cannula and the guide bushing further simplifies lead introduction tools and reduces the number of steps in the lead introduction procedure.

The lead is introduced into an anatomical target as described in connection with FIGS. 33A-B. From the partially introduced position of FIG. 40A the lead assembly is advanced toward the anatomical target until the stylet handle arrives at the stop bushing. The stop bushing position is set so that when stylet handle 45 is at the stop bushing, the distal tip of the lead is at the desired initial location along the insertion trajectory, e.g., just above a predetermined location of the anatomical target in the brain.

Once at the desired initial location, the stylet handle is coupled to the stop bushing (e.g., by clamping screw 150). The lead can now be incrementally advanced toward the target using a fine motion of the stop holder or using a microdrive (not shown) attached to the stop holder. Once an efficacious placement of the lead is accomplished, stop holder 133 is locked in the instrument carrier of the stereotactic arc (FIG. 32B) thus immobilizing stop bushing 165.

A fully localized lead is shown in FIG. 40B. The stylet spacer and the stylet are removed using a procedure similar to that described in connection with FIG. 33B. Spacer handle 46 is uncoupled from the lead (e.g., by unclamping screw 145) and the spacer is removed by pulling on the spacer handle while the immobilized stylet keeps the lead from retracting. The removal of the spacer creates a radial clearance 168 between the cable and the stylet (FIG. 40C). The radial clearance allows subsequent removal of the stylet without generating drag or traction on the lead.

The stylet is removed by unlocking stop holder 133 from the instrument holder of the stereotactic arc and retracting the stop holder in the direction indicated by the arrows in FIG. 40C. Alternatively, the stylet can be removed by unlocking stylet handle 45 from the stop bushing and pulling on the stylet handle (as indicated by the arrows in FIG. 40D). As distal end 44 of the stylet separates from shoulder 33, the collar formed by the stepped body portion 32 helps to stabilize the electrode terminal in the anatomical target.

FIGS. 41-43—Lead with External Stylet for Introduction Using Conventional Cannula The leads and lead introduction tools disclosed above utilize an external stylet and a cannula or a stylet guide that is always kept external to the brain. However, a lead system with an external stylet can also be advantageous when it is introduced into the target tissue utilizing a conventional brain cannula, i.e., a cannula that is pre-inserted into the brain. In particular, the advantages of the stranded conductor cable can be realized and the external stylet can be used to immobilize the lead when the cannula is being removed and when the lead is being anchored at the burr hole. After the lead is anchored, the introduction tools can be removed without dislodging the lead.

FIG. 41 shows an external stylet assembly adapted for use with a cannula inserted into the brain. Stylet 41 has a permanently attached handle 170 comprising a coupling mechanism for disengageably attaching the stylet assembly to the lead. The exemplary coupling consists of screw 145 and leaf spring insert 146 but other couplings such as a set screw, a quick release spring coupling, or a spring plunger coupling can be used.

FIG. 42 shows a lead embodiment adapted for use with an external stylet and a brain entering cannula. The electrode terminal 23, the connector terminal 26, and the cable 29 can be similar to those disclosed above under corresponding numerals. The cable comprises a reinforced portion 171, a stepped portion 172, and main cable portion 29. The main cable portion can be constructed as shown in FIGS. 3A-D and the reinforced cable portion can be constructed as shown in FIGS. 4A-B. The construction of stepped cable portion 172 can be similar to the main portion of cable 29, but with a thicker outer jacket. Other cable constructions, including those utilizing coiled conductors can be alternatively used.

The stepped cable body has a proximally facing shoulder 173 which provides a bearing surface for the distal end 44 of the stylet. The combined length of the electrode terminal 23 and cable portions 171 and 172 is greater than the maximum depth of any anticipated target in the brain. This assures that shoulder 173 is always external to the brain.

In FIG. 43, the stylet assembly is shown assembled with the lead. The proximal end of the lead is inserted into the central lumen of the tubular stylet 41 from the stylet's distal end until shoulder 173 is in contact with distal end 44 of the stylet. After applying a slight tension to the cable, the cable is coupled to the stylet handle by clamping screw 145. Cable portions 171 and 172 and the outside diameter of the stylet have substantially the same outside diameter sized for a sliding fit in the cannula. If desired, the outside diameter of the reinforced electrode terminal can also be sized for sliding fit in the cannula. The stylet may have graduated marks 141 to allow monitoring of the lead's advancement into the brain by reference to the top surface of the stop bushing or other stationary reference.

FIGS. 44A-C—Lead Introduction using External Stylet and Conventional Cannula FIGS. 44A-C are partial cross-sectional views of a lead and lead introduction tools utilizing a cannula 175. Guide holder 132 and stop holder 133 slidably connect to the instrument carrier of the stereotactic arc as shown in FIG. 32A. The cannula is pre-inserted into the brain so that the distal end of the cannula is a desired distance from the anatomical target in the brain. The lead is subsequently introduced through the stop bushing and the cannula (FIG. 44A) until the stylet handle arrives in the stop bushing (FIG. 44B). The lead is now at the desired initial position above the anatomical target. The stylet handle is locked in the stop bushing and the lead can be gradually advanced toward the target as previously discussed.

After the lead is successfully localized in the target tissue, the stop bushing is immobilized. Since the stylet handle 170 is clamped in a stationary stop bushing 138 with screw 150, the stylet is also immobilized. The cannula is raised above the cranium line 136 as shown in FIG. 44C to allow anchoring of the lead at the exit from the burr hole (burr hole 135 is shown in FIG. 32A). The distal end of the stylet remains in contact with the lead's shoulder, thus preventing the lead from retracting when the cannula is being raised and when the lead is being anchored in the body tissue.

After the lead is anchored, the stylet handle can be released from the stop holder by unclamping screw 150 and the stylet can be removed by pulling on the stylet handle. Following the removal of the stylet, the cannula and the remaining tools can be removed without disturbing lead localization (the lead is already anchored).

FIGS. 45A-C—Lead Introduction Tools for Iso-Diametric Leads

Lead introduction tools are disclosed for introduction of iso-diametric leads with minimal manual handling of the lead. In the embodiment of FIGS. 47A-B, the stylet assembly is coupled to a cannula thus allowing the cannula to travel with the lead during lead introduction.

FIGS. 45A-C are partial cross-sectional views of a lead introduction system similar to that in FIGS. 44A-C, adapted for use with an iso-diametric lead having an internal stylet. Referring to FIG. 45C, the lead has an electrode terminal 180 at the distal end and a connector terminal 181 at the proximal end, connected by a cable 182. The electrode terminal is reinforced with a built-in stylette 183. Alternatively, the electrode terminal can have a reinforcing tube if a construction similar to that in electrode terminal 23 is used. The connector terminal and a portion of the cable have a lumen 184 (shown occupied by stylet 185 in FIG. 45C). The lumen may be formed by coiled conductors which are commonly used in iso-diametric leads. Alternatively, a lumen may be provided in insulating body 36 (FIG. 3C) or core 37 (FIG. 3D).

The stylet assembly comprises an internal stylet 185 and a stylet handle 186. The stylet is inserted into the lumen of the lead until the distal end of the stylet is in contact with the bottom of the lumen 184. A portion 187 of the cable does not receive the stylet and therefore remains flexible. The stylet handle is coupled to the lead with screw 145 or other coupling means, e.g., a quick release spring loaded coupling such as shown in FIG. 35B. The proximal end of the stylet is captivated in stylet handle 186.

After the lead is successfully localized in the anatomical target, the cannula is raised (FIG. 45C) and the lead is anchored while the immobilized stylet holds the lead from retracting. The stylet remains in the lead when the lead is being anchored. Since portion 187 of the lead does not contain the stylet, the lead can be anchored at the exit from the burr hole while the stylet is present in the lead. After the lead is anchored, the stylet and the remaining introduction tools can be remove without dislocation of the lead.

This is in contrast to the prior art where a lead holder (an additional device attached to the stereotactic instrument) is used to immobilize the proximal end of the lead before the cannula is raised. The internal stylet of prior art must be removed before the lead is anchored, which may cause a dislodgment of the lead electrodes due to the traction between the lead and the cannula. Consequently, manual holding of the lead at the exit from the burr hole is required in order to remove the stylet and anchor the lead.

FIGS. 46A-B—Lead Introduction Tools with Connector Interface to External Unit FIGS. 46A-B show a variation of the lead introduction system of FIGS. 45A-C, further comprising an external connector 188 having resilient contacts 189 for operatively connecting the lead to an external unit (e.g., a test stimulator or a screening unit) during lead introduction. A stylet handle 190 is adapted to receive the external connector and to align the resilient contacts with the corresponding contacts 191 of the lead's connector terminal. Clamping screw 145 completes the connection of the lead to the external unit and couples the lead to the stylet handle. (If an external connector is not used a dummy insert can be used to couple the stylet handle to the lead.)

Since the lead is coupled to the handle over the connector terminal, the lead contacts carry the clamping load and thus prevent compressing of the lead's insulating body. The stylet is therefore not constrained in the lead and, if desired, can be removed without disconnecting the external connector from the lead contacts. This allows the external connector to remain connected to the lead when the stylet is being removed. Once the lead is anchored and the therapeutic effect is confirmed, the connector can be disconnected and the stylet can be removed.

Another advantage of clamping the lead to the stylet over the connector terminal is that, when the stop bushing is locked in place, the proximal end of the lead is immobilized without restricting stylet removal. This allows use of a conventional iso-diametric lead with a full length stylet (FIG. 1A-B, prior art). The stylet can be raised to allow lead anchoring while the proximal end of the lead is immobilized in the stylet handle.

FIGS. 47A-B—Lead Introduction Tools for Short Leads with Extended Internal Stylet FIGS. 47A-B show cross-sectional views of another embodiment of a lead introduction system adapted for use with a lead utilizing a proximally extended internal stylet. The system can be employed with very short leads. In FIG. 47A the lead is fully localized. In FIG. 47B the cannula is raised to allow the lead to be anchored at the burr hole.

The lead introduction system comprises a stylet 194, a stylet handle 195, a stylet holder 196, and guide bushing 165. The bushing comprises a locking means adapted to receive and lock the stylet handle.

The stylet handle has a coupling means adapted to couple the stylet to the lead. Screw 197 couples the stylet to the handle and screw 145 couples the handle to the lead. When screws 145 and 197 are clamped, the stylet is coupled to the lead. Guide bushing 165 is locked in stop holder 133 and serves as a guide for the cannula and a depth stop for the cannula and the lead-stylet assembly.

Stylet holder 196 is rigidly attached to a stationary stereotactic arc or other stationary frame or support. The stylet holder has a clamping screw 198 adapted to lock and immobilize the stylet in the stylet holder. When the lead is being introduced (advanced or retracted), screw 198 is unclamped and the stylet can move freely in the stylet holder. When the introduction tools are being removed, screw 198 is clamped and the stylet is immobilized.

The proximal portion 199 of stylet 194 is extended out of the lead to allow retraction of the introduction tools as shown in FIG. 47B. For short leads, the proximal portion of the stylet can be extended to allow raising the tools until proximal connector terminal 181 is exposed and accessible for connecting an external pulse generator or a screening unit. Proximal portion 199 of the stylet can have a larger diameter than the stylet portion inserted into the lead.

The lead introduction and disassembly of the tools may comprise the following steps:

(a) Set stop bushing at a desired elevation over the cranium by locking stop holder 133 in the stereotactic instrument holder.

(b) Pre-insert the cannula into the brain.

(c) Insert lead-stylet assembly, with screws 145 and 197 clamped, into the cannula lumen and advance the lead through the cannula until the stylet handle is received in the stop bushing. The electrode terminal extends from the cannula and the electrodes are at the desired initial position.

(d) Couple the stylet handle to the stop bushing, e.g., by clamping screw 150. The cannula is captivated between the stylet handle and the stop bushing and also becomes coupled to the stop bushing.

(e) Place the stylet holder over the proximal end of the stylet and attach the stylet holder to the stereotactic arc. Screw 198 is unclamped.

(f) Incrementally advance the lead using a fine motion of the stop holder to localize the lead in the anatomical target. The lead, the stylet, and the cannula advance and retract in unison.

(g) After lead is successfully localized and therapeutic effect is confirmed, lock the proximal end of the stylet in the stylet holder, e.g., by clamping screw 198. The stylet is now immobilized.

(h) Decouple the stylet handle from the lead and from the stylet, e.g., by unclamping the screws 145 and 197 respectively.

(i) Raise the introduction tools to expose the lead exiting from the burr hole while the immobilized stylet holds the lead from retracting. Clamp the lead handle to the stylet by clamping screw 197 to hold the tools in the raised state.

(j) Anchor the lead with a suitable anchor.

(k) Detach the stylet holder from stereotactic arc and remove the tools.

Alternatively, the cannula may be permanently attached to the lead's handle (as is external stylet in FIG. 40A). In such case, the lead and the cannula are pre-assembled together so that the electrode terminal extends from the distal end of the cannula by a fixed distance. All electrodes are exposed, as shown in FIG. 47A. The lead and cannula are coupled and are introduced into the brain concurrently. The reinforced distal end of the lead acts as an obturator (a tool that is used to close the distal opening of the cannula when the cannula is pre-inserted into the brain).

The cannula may also be adjustably coupled to the lead's handle. In the first position, only the distal tip of the lead extends from the cannula and acts as an obturator when the cannula is inserted into the brain. Once the cannula is in the desired position above the anatomical target, the coupling is adjusted so that the electrode terminal emerges from the cannula and all electrodes become exposed. During final localization of the lead, the cannula travels with the lead.

In the step (i) of the above procedure, the cannula can be raised until the connector terminal 181 is fully exposed and accessible for connecting to an external pulse generator or a screening unit. This allows verification of therapeutic effect after the lead is anchored. If a micro-dislodgement occurred that affected the therapeutic efficacy a repositioning of the lead can be attempted because the stylet never left the lead. The lead anchor can be removed and the cannula may be lowered into the tissue. The stylet handle is then re-coupled to the lead to allow adjustment of the lead position.

Advantages

From the description above, a number of advantages of various embodiments of the disclosed leads will be evident:

(a) Externalized stylet allows the conductor cable to have a small diameter and a desirably short length, improving lead management within implantation site.

(b) A variety of conductor and cable constructions can be used to provide flexibility and high crush resistance.

(c) The use of inserts to connect wires to electrodes provides robust, small dimensioned electrode terminals which are economical to fabricate and are suitable for small anatomical targets that require lead placement with high spatial resolution.

(d) A reinforced electrode terminal can be introduced into the brain without a brain-entering cannula.

(e) The distal portion of the lead body can have a collar which helps to stabilize the electrode terminal in the anatomical target.

(f) The guiding cannula is not inserted into the brain, thus eliminating disruption of brain tissue due to introduction of the cannula. Some embodiments of leads with external stylet assembly can be implanted without using a cannula.

(g) Lead dislodgment due to removal of the stylet is minimized. A stylet holds the lead from retracting when a spacer is being removed. Removal of the spacer creates a radial clearance that allows traction-free removal of the stylet.

(h) The disclosed leads and introduction tools are compatible with standard stereotactic instrumentation and lead localization procedures.

(i) A short interface between the lead and the introduction tools minimizes placement errors by reducing traction-induced forces on the lead when the lead is introduced and when the stylet and introduction tools are removed.

(j) The stylet assembly cooperates with the stereotactic instrumentation to positively control lead advancement and to minimize direct manual handling of the lead.

(k) The externalized stylet can have graduated marks to index insertion depth. Unlike marks on a lead body, the marks on the stylet are not subject to stretching.

(l) Optionally, a brain-entering cannula can be used. In such case, the externalized stylet serves as a built-in lead holder when the cannula is raised and the lead can be anchored before the stylet is removed.

RAMIFICATIONS AND SCOPE

While the above description contains many specificities, these should not be construed as limitations on the scope of the invention, but as exemplifications of some present embodiments thereof. Many other ramifications and variations are possible within the teachings of the invention. For example, the disclosed leads and introduction tools are applicable to a variety of implantable systems having sensing and/or stimulation leads or other similarly shaped components such a catheter.

Lead designs and lead introduction tools disclosed in the context of brain stimulation are also applicable for introducing leads, catheters, or similarly shaped devices into other parts of the body.

While the leads and introduction tools have been described by means of specific embodiments, numerous modifications and variations known to those skilled in the art or disclosed may be employed without departing from the scope of the invention set forth in the claims. For example, the materials, dimensions, shapes, and sizes of all parts may be adapted to a particular need.

All materials referenced in connection with implantable leads, devices, and other implantable accessories are biocompatible and accepted for implantation in the human brain or other living tissue. The term "biocompatible" or "implantable grade" is therefore implicit when these materials are listed.

The number of conductors typically corresponds to the number of electrodes but may be different depending on the desired connectivity.

The leads are shown having four electrodes and four conductors but a single electrode or any number of electrodes can be employed. In any case, the lead will have at least one electrode at the distal end which is electrically connected to at least one contact at the proximal end.

Additional electrodes may be used so that the electrode or electrodes providing optimum therapeutic effect could be selected. Redundant electrodes can also be used to adjust the therapy non-invasively, without requiring a corrective surgery, when the therapy through the originally assigned electrodes becomes ineffective, e.g., due to migration of the lead.

The outer surface of the electrodes can be cylindrical, convex or barrel-shaped, spherical, or may have other smooth shape to provide desired stimulation. The electrodes can be segmented, e.g., providing two independent semi-circular electrodes in place of a single ring electrode, so that the stimulation could be activated on one side but turned off on the other side.

The tip electrode can be adapted for use as a recording or testing electrode.

The contacts and electrodes may be substantially similar and the constructions of the electrode terminal and the contact terminal can be used interchangeably.

The construction of the electrode terminal and the conductor-to-electrode termination methods can be applied to a wide variety of leads such as cardiac pacing leads and electrophysiologic testing leads.

The stylet may be of a multi-piece construction, with two or more pieces joined by welding, press-fit, or another method.

The internal stylet may have a non-circular cross-section or may have a stepped diameter.

The lumen for internal stylet need not be centrally disposed and need not have a circular cross-section.

Thus the scope should be determined, not by the examples or specifics given, but by the appended claims and their legal equivalents

I claim:

1. An implantable electrical lead having an elongated body having a proximal end and a distal end, said elongated body having a stepped outside diameter and a stepped body portion having a proximally facing shoulder formed by said stepped outside diameter, said lead comprising:
   (A) an electrode terminal at said distal end of said lead, said electrode terminal comprising a body and at least one electrode embedded in said body;
   (B) a connector terminal at said proximal end of said lead, said connector terminal having a body and at least one contact embedded in said body;
   (C) a conductor cable between said electrode terminal and said connector terminal, said cable having an insulating jacket and at least one conductor encased in said jacket, said conductor electrically connecting said electrode to said contact;
   (D) a removable stylet assembly comprising a stylet and a stylet spacer, said stylet spacer occupying the radial space between said stylet and said lead, said stylet having a distal end, a proximal end, and a central lumen, said lumen accommodating said lead and said stylet spacer so that said stylet and said stylet spacer are external to said lead;
   whereby after said lead is implanted in an anatomical target, said stylet spacer can be removed while said distal end of said stylet is bearing on said shoulder to hold said lead from retracting, and wherein the removal of said stylet spacer clears the radial space between said lead and said stylet, whereby said stylet can be subsequently removed without causing traction on said lead.

2. The implantable electrical lead of claim 1 wherein said body of said electrode terminal and a portion of said lead extending from said electrode terminal have a contiguous reinforcing means, whereby said reinforcing means cooperates with said stylet assembly to minimize flexing and tilting of said electrode terminal with respect to said stylet assembly.

3. The lead of claim 2 wherein said reinforcing means is a centrally disposed stylette, wherein said stylette material is selected from the group consisting of platinum, platinum-iridium, stainless steel, titanium, a titanium alloy, a reinforced polymer, and any combination thereof.

4. The implantable electrical lead of claim 2 wherein said reinforcing means is a reinforcing tube and said at least one conductor of said cable extends within said reinforcing tube toward said at least one electrode.

5. The implantable electrical lead of claim 4 wherein said reinforcing tube has a lengthwise slot, said slot providing a passage for each said conductor from within said tube toward said respective electrode.

6. The implantable electrical lead of claim 4 wherein said reinforcing tube material is selected from the group consisting of platinum, platinum-iridium, stainless steel, titanium, a titanium alloy, a polymer, and any combination thereof.

7. The implantable electrical lead of claim 4, wherein said electrode terminal further comprises a conductive tip, said tip joined to said reinforcing tube and forming a tip electrode, said tip electrode being electrically connected to said respective contact.

8. The implantable electrical lead of claim 4 further comprising an interliner sleeve having a lengthwise slit, said slit providing a passage for each said conductor from within said tube toward said respective electrode, said interliner sleeve being interposed between said reinforcing tube and said at least one electrode, wherein said interliner sleeve insulates said electrode from said reinforcing tube and maintains concentricity between said electrode and said reinforcing tube.

9. The implantable electrical lead of claim 1 wherein said connector terminal has a stiffening core comprising a channel, said channel accommodating said at least one conductor of said cable and allowing said at least one conductor to be joined and electrically connected to said respective contact.

10. The implantable electrical lead of claim 1 wherein the axial length of each conductor is greater than the axial length of said jacket of said cable, so that no axial tension is applied to said conductor when said jacket is stretched to a length not exceeding the length of said conductor.

11. The implantable electrical lead of claim 1 wherein said conductor of said cable has a stranded construction comprising a plurality of conductive wires twisted or helically wound together.

12. The implantable electrical lead of claim 11 wherein said cable further comprises a center core, each said conductor of said cable being helically wound onto said center core.

13. The implantable electrical lead of claim 12 wherein said center core material is selected from the group consisting of elastomer, aramid fiber, polyimide, and polytetrafluoroethylene.

14. The implantable electrical lead of claim 1 wherein the outside diameter of said electrode terminal is smaller than the outside diameter of said stepped body portion of said lead.

15. The implantable electrical lead of claim 1 wherein said stepped body portion of said lead forms a collar, whereby said collar helps to stabilize the position of said electrode terminal within said anatomical target.

16. The implantable electrical lead of claim 1 wherein said body of said electrode terminal and said stepped body portion of said lead are made from a material selected from the group consisting of silicone rubber, polyurethane, silicone-urethane copolymer, and polyetheretherketone.

17. The implantable electrical lead of claim 1 wherein said stylet has a handle on its proximal end and said distal end of said stylet is in contact with said shoulder of said stepped portion of said lead.

18. The implantable electrical lead of claim 17 wherein said stylet spacer has a proximal end and a distal end, said stylet spacer further having a handle on its proximal end.

19. The implantable electrical lead of claim 18, further including a coupling mechanism between said spacer handle and said lead, wherein said coupling mechanism is selected from the group consisting of a clamp screw coupling, a quick-release spring coupling, a clamp screw over interposed spring coupling, a clamp screw over insert coupling, and any combination thereof, wherein said spacer handle is disengageably coupled to said lead by said coupling mechanism.

20. The implantable electrical lead of claim 18, further comprising a retention mechanism between said stylet spacer and said lead, wherein said retention mechanism is selected from the group consisting of an interference fit, a friction fit, a shearable adhesive interface, a spring action fit, and any combination thereof, wherein said lead is retentively engaged with said stylet spacer by said retention mechanism.

21. The implantable electrical lead of claim 18 wherein said stylet spacer comprises at least two spacer segments, each spacer segment having a substantially arcuate cross-section, whereby said lead is coupled to said spacer by clamping said stylet segments when said stylet is installed over said spacer.

22. The implantable electrical lead of claim 18 wherein said stylet handle has a stylet spacer disengagement mechanism comprising a driving nut, said stylet spacer being releasable from said lead by rotating said driving nut while said stylet handle is immobilized.

23. The implantable electrical lead of claim 18 wherein said stylet is captivated on said lead between said shoulder of said lead and said handle of said stylet spacer.

24. The implantable electrical lead of claim 1 wherein the outside diameter of said stylet is substantially equal to the outside diameter of said stepped body portion of said lead, whereby both said stylet and said stepped body portion can be guided continuously in a lumen of a cannula.

25. The implantable electrical lead of claim 1 wherein said stylet has graduated marks on its outer surface.

26. The implantable electrical lead of claim 1 wherein said stepped body portion comprises a tubular sheath extending proximally from said body of said electrode terminal, said sheath having a wall, an outer surface, an opening, and an outer end, said outer end providing said shoulder, wherein said stylet spacer is inserted into said opening of said sheath.

27. The implantable electrical lead of claim 26 wherein said stylet spacer is in a retentive contact with said wall of said sheath.

28. The implantable electrical lead of claim 1, further comprising a conductive insert, said conductor being joined and electrically connected to said insert and said insert being joined and electrically connected to said electrode.

29. The implantable electrical lead of claim 28 wherein said insert is arcuate and has an outer surface, said electrode further having a cross-hole and an inner surface, said cross-hole having an edge, said inner surface of said electrode locating said outer surface of said insert, said outer surface of said insert being joined to said edge of said cross-hole.

30. The implantable electrical lead of claim 28 wherein said insert is arcuate and has an outer surface, said electrode having an inner surface and a rim, said inner surface locating said outer surface of said insert, said outer surface of said insert being joined to said rim of said electrode.

31. The implantable electrical lead of claim 28 wherein said insert has an outer surface and an edge, said electrode has a cutout, said cutout having an edge that is complementary to said edge of said insert, said perimeter edge of said insert being joined to said complimentary edge of said cutout of said electrode.

32. The implantable electrical lead of claim 28 wherein said insert is button shaped and has a substantially round weld side, said electrode further has a cross-hole adapted to accommodate said substantially round weld side of said insert, said insert being joined to said electrode at complementary edges of said weld side and said cross-hole.

33. The implantable electrical lead of claim 28 wherein said insert is tubular and has a body portion, said electrode further has an arcuate cutout and a cross-hole, said cross-hole having an edge, said arcuate cutout locating said body of said tubular insert, said body of said insert being joined to said edge of said cross-hole.

34. The implantable electrical lead of claim 1 wherein said electrode terminal has a stiffening core comprising a channel, said channel accommodating said at least one conductor of said cable and allowing said conductor to be joined and electrically connected to said respective electrode.

35. A lead introduction system for introducing an electrical lead into an anatomical target within the human body, said system comprising:
   (A) an implantable electrical lead having an elongated body having a proximal end and a distal end, said elongated lead body having a stepped outside diameter and a stepped body portion having a proximally facing shoulder formed by said stepped outside diameter, said lead comprising an electrode terminal at said distal end of said lead, a connector terminal at said proximal end of said lead, and a conductor cable connecting said electrode terminal to said contact terminal, said electrode terminal and at least a portion of said cable extending from said electrode terminal comprising a contiguous reinforcing means;
   (B) a removable stylet assembly comprising a stylet and a stylet spacer, said stylet having a central lumen, said lumen accommodating said cable body and said stylet spacer so that said stylet and said stylet spacer are external to said lead; said stylet having a proximal end, a distal end, and a handle, said handle being attached to said proximal end of said stylet;
   (C) a stop bushing having a lumen and a locking means arranged to lock said stylet handle to said stop bushing when said stylet handle arrives at said bushing after said lead is advanced through said lumen to a desired initial position above the anatomical target;
   whereby after said stylet handle is locked in said stop bushing, said lead can be advanced or retracted with said stop bushing when said lead is being localized in the anatomical target and, after said lead is successfully localized, said stop bushing and said stylet can be immobilized to hold said lead from retracting when said stylet spacer is being removed, and wherein the removal of said stylet spacer clears the radial space between said lead and said stylet, whereby said stylet can be subsequently removed without causing traction on said lead.

36. The lead introduction system of claim 35 wherein said stylet spacer has a proximal end, a distal end, and a handle attached to said proximal end.

37. The lead introduction system of claim 35, further comprising a stationary instrument carrier having a stop holder adapted to hold said stop bushing aligned with a lead insertion trajectory, said stop holder being slidably mounted in said instrument carrier in a manner that allows a translation of said stop holder along said lead insertion trajectory and further allows immobilizing said stop holder in said instrument carrier.

38. The lead introduction system of claim 37 wherein said stop bushing is adapted to (a) guide said lead with said stylet assembly through said lumen of said stop bushing, (b) stop said lead at a desired initial location along said insertion trajectory, (c) lock said stylet handle and translate with said lead along said insertion trajectory, and (d) immobilize said stylet with said lead when said stylet spacer is being retracted.

39. The lead introduction system of claim 37, further comprising a guide bushing and a guide holder, said guide holder slidably mounted in said instrument carrier and adapted to hold said guide bushing aligned with said lead insertion trajectory.

40. The lead introduction system of claim 39 wherein said guide bushing is adapted to guide said lead with said stylet assembly when said lead is being introduced into said anatomical target.

41. The lead introduction system of claim 39, further comprising a cannula, said cannula held in said guide bushing, so that said cannula can be used to guide said stylet with said lead when said lead is being introduced into said anatomical target, wherein said anatomical target is in the brain and wherein said cannula is kept outside the brain when said lead is being introduced.

42. The lead introduction system of claim 37, further comprising a stereotactic frame having a stereotactic arc, said instrument carrier being rigidly but adjustably attached to said stereotactic arc.

43. The lead introduction system of claim 35 wherein said locking means of said stop bushing is selected from the group consisting of a screw clamp locking means, a quick-release locking means, and a spring plunger locking means.

44. An implantable electrical lead system comprising an elongated body having a proximal end and a distal end, said elongated body having a stepped outside diameter, said lead comprising:
- (A) an electrode terminal at said distal end of said lead, said electrode terminal comprising a body and at least one electrode embedded in said body;
- (B) a stepped body portion having a proximally facing shoulder formed by said stepped outside diameter;
- (C) a connector terminal at said proximal end of said lead, said connector terminal having a body and at least one contact embedded in said body;
- (D) a conductor cable between said electrode terminal and said connector terminal, said cable having an insulating jacket and at least one conductor encased in said jacket, said conductor electrically connecting said electrode to said contact;
- (E) a removable, substantially tubular stylet, said stylet having a proximal end, a distal end, and a central lumen; said lumen accommodating said cable so that said stylet is external to said elongated body of said lead and has its distal end in contact with said proximally facing shoulder of said stepped portion of said lead;

wherein said body of said electrode terminal and at least a portion of said conductor cable extending from said electrode terminal have a contiguous reinforcing means, whereby said reinforcing means minimizes flexing and tilting of said electrode terminal with respect to said portion of said conductor cable adjacent to said electrode terminal, and whereby said distal end of said stylet is bearing on said shoulder of said lead when said lead is being introduced into an anatomical target in the human body, and whereby said stylet holds said lead from retracting when a cannula used to guide said lead to the anatomical target is being removed; and wherein said lead system further has a radial clearance between said stylet and said elongated body of said lead, whereby after said lead is implanted in the anatomical target, said stylet can be removed without causing traction on said lead.

45. The implantable electrical lead of claim 44 wherein said reinforcing means is a reinforcing tube and said at least one conductor of said cable extends within said reinforcing tube toward said at least one electrode.

46. The implantable electrical lead of claim 45 wherein said reinforcing tube has a lengthwise slot, said slot providing a passage for each said conductor from within said tube toward said respective electrode.

47. The implantable electrical lead of claim 46 further comprising an interliner sleeve having a lengthwise slit, said slit providing a passage for each said conductor from within said tube toward said respective electrode, said interliner sleeve being interposed between said reinforcing tube and said at least one electrode, wherein said interliner sleeve insulates said electrode from said reinforcing tube and maintains concentricity between said electrode and said reinforcing tube.

48. The implantable electrical lead of claim 44 wherein said connector terminal has a stiffening core comprising a channel, said channel accommodating said at least one conductor of said cable and allowing said conductor to be joined and electrically connected to said respective contact.

49. The implantable electrical lead of claim 44 wherein said electrode terminal has a stiffening core comprising a channel, said channel accommodating said at least one conductor of said cable and allowing said conductor to be joined and electrically connected to said respective electrode.

50. The implantable electrical lead of claim 44, further comprising a substantially arcuate conductive insert, said conductor being joined and electrically connected to said insert, and said insert being joined and electrically connected to said electrode.

51. The implantable electrical lead of claim 44 wherein said conductor of said cable has a stranded construction comprising a plurality of conductive wires twisted or helically wound together.

52. The implantable electrical lead of claim 44 wherein said body of said electrode terminal and said stepped body portion of said lead are made from a material selected from the group consisting of silicone rubber, polyurethane, silicone-urethane copolymer, and polyetheretherketone.

53. The implantable electrical lead of claim 44 wherein said stylet has a handle at its proximal end, wherein said stylet handle further has a coupling mechanism for disengageably attaching said stylet handle to said lead; whereby when said handle is attached to said lead, said lead can advance and retract in unison with said stylet when said lead is being introduced into said anatomical target.

54. The implantable electrical lead of claim 53 wherein said coupling mechanism is selected from the group consisting of a clamp screw coupling, a quick-release spring coupling, a clamp screw over interposed spring coupling, a clamp screw over insert coupling, and any combination thereof.

55. The implantable electrical lead of claim 44 wherein the outside diameter of said stylet is substantially equal to the outside diameter of said stepped body portion of said lead, whereby both said stylet and said stepped body portion of said lead can be guided continuously in a lumen of a cannula.

56. The implantable electrical lead of claim 44 wherein said stylet has graduated marks on its outer surface.

57. The implantable electrical lead of claim 44, further comprising a retention mechanism between said stylet and said lead, wherein said retention mechanism is selected from the group consisting of an interference fit, a friction fit, a shearable adhesive interface, a spring action fit, and any combination thereof, and wherein said lead is retentively engaged with said stylet by said retention mechanism.

58. An implantable electrical lead system of claim 44 wherein said electrode terminal and said stepped body portion have a predetermined combined length that is greater than the depth of the anatomical target in the body tissue, whereby said lead can be anchored at the exit from the body tissue before said stylet is removed.

* * * * *